(12) United States Patent
Sadeghi

(10) Patent No.: US 11,183,300 B2
(45) Date of Patent: Nov. 23, 2021

(54) METHODS AND APPARATUS FOR PROVIDING GUIDANCE TO MEDICAL PROFESSIONALS

(71) Applicant: Nuance Communications, Inc., Burlington, MA (US)

(72) Inventor: Sepehr Sadeghi, Lexington, MA (US)

(73) Assignee: Nuance Communications, Inc., Burlington, MA (US)

( * ) Notice: Subject to any disclaimer, the term of this patent is extended or adjusted under 35 U.S.C. 154(b) by 682 days.

(21) Appl. No.: 13/911,023

(22) Filed: Jun. 5, 2013

(65) Prior Publication Data

US 2014/0365232 A1    Dec. 11, 2014

(51) Int. Cl.
| | |
|---|---|
| *G16H 50/20* | (2018.01) |
| *G06F 40/30* | (2020.01) |
| *G06F 40/166* | (2020.01) |
| *G06F 40/143* | (2020.01) |
| *G16H 15/00* | (2018.01) |
| *G10L 15/00* | (2013.01) |

(52) U.S. Cl.
CPC ........... *G16H 50/20* (2018.01); *G06F 40/143* (2020.01); *G06F 40/166* (2020.01); *G06F 40/30* (2020.01); *G10L 15/00* (2013.01); *G16H 15/00* (2018.01)

(58) Field of Classification Search
CPC ........ G06Q 50/22; G06Q 50/24; G06Q 50/20; G06F 19/322; G06F 19/323–327; G06F 19/345; G06F 19/3487; G06F 17/24; G06F 17/2247; G06F 17/2785; G06F 19/00; G06F 19/32; G16H 10/00; G16H 10/60; G16H 50/00; G16H 70/00; G16H 70/20; G10L 15/00

USPC ........................................................ 705/2, 3
See application file for complete search history.

(56) References Cited

U.S. PATENT DOCUMENTS

| | | | |
|---|---|---|---|
| 4,696,039 A | | 9/1987 | Doddington |
| 5,031,113 A | | 7/1991 | Hollerbauer |
| 5,051,924 A | | 9/1991 | Bergeron et al. |

(Continued)

FOREIGN PATENT DOCUMENTS

| | | | | |
|---|---|---|---|---|
| CA | 2831354 A1 | * | 10/2012 | ............ G06F 40/55 |
| DE | 19533541 C1 | | 3/1997 | |

(Continued)

OTHER PUBLICATIONS

International Search Report and Written Opinion for PCT/US2014/041041 dated Nov. 21, 2014.

(Continued)

*Primary Examiner* — Jason S Tiedeman

(74) *Attorney, Agent, or Firm* — Wolf, Greenfield & Sacks, P.C.

(57) ABSTRACT

Method and apparatus for providing guidance to medical professionals. In some embodiments, at least one natural language understanding engine is used to analyze at least one narrative provided by a radiologist in connection with a study of one or more medical images. One or more decision rules are applied to one or more facts extracted by the at least one natural language understanding engine from the at least one narrative, and a result of applying the one or more decision rules to the one or more facts extracted from the at least one narrative is used to provide guidance to the radiologist.

20 Claims, 11 Drawing Sheets

```
                                                                 ,905        ,- 900
                                                                 ---         /
     CLINICAL INFORMATION: Patient is a | 65 female.|

TECHNIQUE: CT scan of the chest without intravenous contrast.

FINDINGS: There is no significant axillary or mediastinal
     adenopathy. No gross hilar adenopathy is noted. The heart is
     normal in size. There is no pericardial effusion. There are
     coronary artery calcifications. No pleural effusion is noted. 910A
     |A 6 mm nodule is noted laterally in the left lower lobe| on
     series 5, image 31 and 32. There is also a | stable 2 mm nodule |
     ,|in the right middle lobe| on series 5, image 29. The 2 mm
915A-' nodule which was seen along the right major fissure on the
     previous examination is not well delineated on this
     examination due to atelectatic changes in this area.
                                                                       910B
     IMPRESSION:  1. |INDETERMINATE NODULE IN THE LEFT LOWER LOBE|
     AND |STABLE NODULE IN THE RIGHT MIDDLE LOBE.|  4. |FOLLOW UP CT|
     |IS RECOMMENDED IN 18 MONTHS| TO ASSESS STABILITY OF THE
     PULMONARY NODULES.  END OF IMPRESSION
                                                          915B       920
```

(56) References Cited

U.S. PATENT DOCUMENTS

| | | | |
|---|---|---|---|
| 5,583,758 A | 12/1996 | McIlroy et al. | |
| 5,680,511 A | 10/1997 | Baker et al. | |
| 5,758,322 A | 5/1998 | Rongley | |
| 5,787,394 A | 7/1998 | Bahl et al. | |
| 5,909,667 A | 6/1999 | Leontiades et al. | |
| 5,987,606 A * | 11/1999 | Cirasole | G06F 17/30867 707/E17.109 |
| 5,999,896 A | 12/1999 | Richardson et al. | |
| 6,003,002 A | 12/1999 | Netsch | |
| 6,073,101 A | 6/2000 | Maes | |
| 6,173,259 B1 | 1/2001 | Bijl et al. | |
| 6,212,498 B1 | 4/2001 | Sherwood et al. | |
| 6,243,722 B1 * | 6/2001 | Day | G06F 17/30899 707/E17.119 |
| 6,307,576 B1 * | 10/2001 | Rosenfeld | G06T 13/205 345/473 |
| 6,360,237 B1 | 3/2002 | Schulz et al. | |
| 6,366,882 B1 | 4/2002 | Bijl et al. | |
| 6,418,410 B1 | 7/2002 | Nassiff et al. | |
| 6,434,547 B1 | 8/2002 | Mishelevich et al. | |
| 6,463,413 B1 | 10/2002 | Applebaum et al. | |
| 6,487,530 B1 | 11/2002 | Lin et al. | |
| 6,567,778 B1 | 5/2003 | Chang et al. | |
| 6,813,603 B1 | 11/2004 | Groner et al. | |
| 7,383,172 B1 | 6/2008 | Jamieson | |
| 7,610,192 B1 * | 10/2009 | Jamieson | G06Q 40/08 704/9 |
| 7,657,832 B1 * | 2/2010 | Lin | G06F 17/2247 715/234 |
| 7,693,705 B1 | 4/2010 | Jamieson | |
| 8,930,218 B1 * | 1/2015 | Oakley | G06F 19/324 705/3 |
| 9,015,098 B1 * | 4/2015 | Crosley | G06F 17/30702 706/46 |
| 9,478,218 B2 | 10/2016 | Shu | |
| 2003/0016850 A1 | 1/2003 | Kaufman et al. | |
| 2003/0115083 A1 | 6/2003 | Masarie et al. | |
| 2005/0033574 A1 | 2/2005 | Kim et al. | |
| 2006/0087674 A1 * | 4/2006 | Lusen | G06Q 10/06 358/1.14 |
| 2006/0241353 A1 * | 10/2006 | Makino | G16H 15/00 600/300 |
| 2006/0282762 A1 * | 12/2006 | Diamond | G06F 17/241 715/235 |
| 2007/0033026 A1 | 2/2007 | Bartosik et al. | |
| 2007/0208567 A1 | 9/2007 | Amento et al. | |
| 2007/0299652 A1 * | 12/2007 | Koll | G06F 17/211 704/9 |
| 2008/0040635 A1 * | 2/2008 | Larcheveque | G06F 17/2247 714/49 |
| 2008/0091690 A1 | 4/2008 | Ellersick et al. | |
| 2008/0231429 A1 * | 9/2008 | Leonard | G06F 17/248 340/146.2 |
| 2008/0255835 A1 | 10/2008 | Ollason et al. | |
| 2009/0187407 A1 * | 7/2009 | Soble | G10L 13/00 704/260 |
| 2009/0192822 A1 * | 7/2009 | Regulapati | G06F 19/325 705/3 |
| 2009/0216558 A1 * | 8/2009 | Reisman | G06F 19/328 705/3 |
| 2009/0287487 A1 * | 11/2009 | Rossman | G06F 19/321 704/235 |
| 2009/0319927 A1 * | 12/2009 | Beeman | G06F 17/24 715/764 |
| 2010/0049756 A1 | 2/2010 | Chemitiganti et al. | |
| 2010/0094836 A1 * | 4/2010 | Duncan | G06Q 30/04 707/705 |
| 2010/0117856 A1 * | 5/2010 | Sonderegger | G06Q 10/06 340/870.02 |
| 2010/0138241 A1 * | 6/2010 | Ruark | G06Q 50/22 705/3 |
| 2010/0145720 A1 | 6/2010 | Reiner | |
| 2010/0153332 A1 * | 6/2010 | Rollins | G06Q 10/10 707/603 |
| 2011/0208540 A1 * | 8/2011 | Lord | G06F 19/325 705/2 |
| 2011/0276343 A1 * | 11/2011 | Lagor | G06F 19/325 705/2 |
| 2012/0095751 A1 * | 4/2012 | Peters | G06F 17/27 704/9 |
| 2012/0150555 A1 * | 6/2012 | Truyen | G06Q 10/04 705/2 |
| 2012/0278243 A1 * | 11/2012 | Frazier | G06Q 30/0278 705/306 |
| 2012/0290323 A1 * | 11/2012 | Barsoum | G16H 15/00 705/3 |
| 2012/0330876 A1 * | 12/2012 | Bryce | G16H 15/00 706/47 |
| 2013/0035961 A1 * | 2/2013 | Yegnanarayanan | G16H 10/60 705/3 |
| 2013/0041685 A1 | 2/2013 | Yegnanarayanan | |
| 2013/0124527 A1 * | 5/2013 | Lee | G06F 7/24 707/737 |
| 2013/0212475 A1 * | 8/2013 | Lee | G06F 17/276 715/261 |
| 2013/0254703 A1 * | 9/2013 | Arling | G06F 3/0484 715/781 |
| 2013/0262364 A1 * | 10/2013 | Verbeek | G06N 5/04 706/46 |
| 2014/0006013 A1 * | 1/2014 | Markatou | G06F 17/3061 704/9 |
| 2014/0149407 A1 | 5/2014 | Qian et al. | |
| 2014/0288920 A1 * | 9/2014 | Proux | G06N 5/025 704/9 |
| 2014/0297269 A1 * | 10/2014 | Qian | G06F 17/30014 704/9 |
| 2014/0344701 A1 * | 11/2014 | Shreiber | G06F 3/04842 715/728 |
| 2019/0046126 A1 | 2/2019 | Owen et al. | |
| 2019/0051376 A1 | 2/2019 | Gallopyn et al. | |
| 2019/0051377 A1 | 2/2019 | Owen et al. | |
| 2019/0051386 A1 | 2/2019 | Owen et al. | |
| 2019/0051387 A1 | 2/2019 | Owen et al. | |
| 2019/0051415 A1 | 2/2019 | Owen | |
| 2019/0066821 A1 | 2/2019 | Owen et al. | |

FOREIGN PATENT DOCUMENTS

| | | | | |
|---|---|---|---|---|
| WO | WO 98/19253 A1 | 5/1998 | | |
| WO | WO 03/040990 A2 | 5/2003 | | |
| WO | WO 2006/058738 | 6/2006 | | |
| WO | WO-2012017418 A1 * | 2/2012 | | G06F 7/24 |
| WO | WO-2013075127 A1 * | 5/2013 | | G06F 19/00 |
| WO | WO-2013176903 A1 * | 11/2013 | | G16H 10/60 |

OTHER PUBLICATIONS

Demner-Fushman et al., What can natural language processing do for clinical decision support? J Biomed Inform. Oct. 2009;42(5):760-72. doi: 10.1016/j.jbi.2009.08.007. Epub Aug. 13, 2009.

Friedman et al., A general natural-language text processor for clinical radiology. J Am Med Inform Assoc. Mar.-Apr. 1994;1(2):161-74.

Serban et al., Extraction and use of linguistic patterns for modelling medical guidelines. Artif Intell Med. Feb. 2007;39(2):137-49. Epub Sep. 11, 2006.

U.S. Appl. No. 11/322,971, filed Dec. 30, 2005*, Zimmerman et al..

U.S. Appl. No. 13/795,886, filed Mar. 12, 2013#, Delaney et al..

U.S. Appl. No. 13/910,997 filed 06-05-20137, Sadeghi.

Florian et al., "A Statistical Model for Multilingual Entity Detection and Tracking," Proceedings of the Human Language Technologies Conference 2004 (HLT-NAACL'04), (2004).

MacMahon et al., Guidelines for management of small pulmonary nodules detected on CT scans: a statement from the Fleischner Society. Radiology. Nov. 2005;237(2):395-400.

Salton et al., "A Vector Space Model for Automatic Indexing," Communications of the ACM, vol. 18, No. 11, Nov. 1975.

(56) References Cited

OTHER PUBLICATIONS

Aronow et al., Ad Hoc Classification of Radiology Reports. Journal of the American Medical Informatics Association. 1999;6(5):393-411.
Bateman et al., The Quest for The Last 5%: Interfaces for Correcting Real-Time Speech-Generated Subtitles. Interactive Posters. CHI 2000. 2 pages.
Birnbaum et al., Report: A Voice Password System for Access Security. AT&T Technical Journal. 1986. 7 pages.
Bisani et al., Automatic Editing in a Back-End Speech-to-Text System. Proceedings of ACL-08: HLT. 2008:114-20.
Heng-Hsou et al., An Event-Driven and Ontology-Based Approach for the Delivery and Information Extraction of E-mails. IEEE. 2000. 103-9.
Hewitt et al., Real-Time Speech-Generated Subtitles: Problems and Solutions. ISCA Archive. 6th International Conference on Spoken Language Processing (ICSLP 2000). 2000. 5 pages.
Mendonca et al., Extracting information on pneumonia in infants using natural language processing of radiology reports. Journal of Biomedical Informatics. 2005;38:314-21.
Naik, Speaker Verification: A Tutorial. IEEE Communications Magazine. 1990:42-8.
Newman et al., Speaker Verifcation Through Large Vocabulary Continuous Speech Recognition. Dragon Systems, Inc. 1996. 4 pages.
Rosenberg, Evaluation of an Automatic Speaker-Verification System Over Telephone Lines. Manuscript received Sep. 9, 1975. The Bell System Technical Journal. 1976;55(6):723-44.
Shvaiko et al., Ontology Matching OM-2008. Papers from the ISWC Workshop. 2008. 271 pages.
Sistrom et al., Managing Predefined Templated and Macros for a Departmental Speech Recognition System Using Common Software. Journal of Digital Imaging. 2001;14(3):131-41.
Soderland et al., Automated Classification of Encounter Notes in a Computer Based Medical Record. MEDINFO 1995 Proceedings. 1995 IMIA. 9 pages.
Sonntag et al., A Discourse and Dialogue Infrastructure for Industrial Dissemination. German Research Center for AI (DFKI). Proceeding IWSDS'10 Proceedings of the Second international conference on Spoken dialogue systems for ambient environments. 2010. 12 pages.
Sonntag et al., RadSpeech's Mobile Dialogue System for Radiologists. IUI'12. 2012. 2 pages.
Suhm, Multimodal Interactive Error Recovery for Non-Conversation Speech User Interfaces. Dissertation. 1998. 292 pages.
Taira et al., Automatic Structuring of Radiology Free-Text Reports. infoRAD. Radiology 2001;21:237-45.
PCT/US2014/041041, Nov. 21, 2014, International Search Report and Written Opinion.

\* cited by examiner

```xml
<case>
  <features>
    <feature name="uniformly_cystic" type="present_absent" default="absent"/>
    <feature name="size" type="numeric"/>
    <feature type="enumeration" name="side">
      <choice name="left_side">Left</choice>
      <choice name="right_side">right</choice>
    </feature>
    <feature type="enumeration" name="size_changed" default_choice="no_priors">
      <choice name="no_priors">
        <synonym>no comparison</synonym>
        <synonym>no history</synonym>
      </choice>
      <choice name="increased">
        <synonym>Larger</synonym>
        <synonym>has grown</synonym>
      </choice>
    ...
  <end_points>
    <end_point id="cyst_no_recommendation">
      <templates>
        <body The nodule found is an adenoma without a history of malignancy.
          There is no history of the size changing, and a higher risk due to {{enter reason here}}.
          A surgery referrral is the follow up recommendation.
        </body>
        <!-- no impression needed -->
      </templates>
      <assertion feature="uniformly_cystic" value="present"/>
    </end_point>
    ...
  <algorithm feature="root">
    <if feature="adrenal_nodule" value="present">
      <if feature="uniformly_cystic" value="present">
        <end_point ref="cyst_no_recommendation"/>
      </if>
      ...
      <else feature="no_known_malignancy">
        <!-- known malignancy is absent -->
        <if feature="size_changed" value="stable">
          <end_point ref="chemical_evaluation"/>
        </if>
```

FIG. 7

CLINICAL INFORMATION: Patient is a 65 female.

TECHNIQUE: CT scan of the chest without intravenous contrast.

FINDINGS: There is no significant axillary or mediastinal adenopathy. No gross hilar adenopathy is noted. The heart is normal in size. There is no pericardial effusion. There are coronary artery calcifications. No pleural effusion is noted. A 6 mm nodule is noted laterally in the left lower lobe on series 5, image 31 and 32. There is also a stable 2 mm nodule in the right middle lobe on series 5, image 29. The 2 mm nodule which was seen along the right major fissure on the previous examination is not well delineated on this examination due to atelectatic changes in this area.

IMPRESSION: 1. INDETERMINATE NODULE IN THE LEFT LOWER LOBE AND STABLE NODULE IN THE RIGHT MIDDLE LOBE. 4. FOLLOW UP CT IS RECOMMENDED IN 18 MONTHS TO ASSESS STABILITY OF THE PULMONARY NODULES. END OF IMPRESSION

FIG. 9

FIG. 10

METHODS AND APPARATUS FOR PROVIDING GUIDANCE TO MEDICAL PROFESSIONALS

BACKGROUND

1. Field

The techniques described herein are directed generally to the field of natural language understanding, and more particularly to techniques for creating and/or processing records in medical settings.

2. Description of Related Art

Medical documentation is an important process in the healthcare industry. Most healthcare institutions maintain a longitudinal medical record (e.g., spanning multiple observations and/or treatments over time) for each of their patients, documenting, for example, a patient's history, encounters with clinical staff, test results, treatments received, and/or plans for future treatment. Such documentation helps to maintain continuity of care for the patient across multiple instances of medical care received by the patient over time. In addition, when an institution's medical records for large numbers of patients are considered in the aggregate, the information contained therein can be useful for many purposes, such as educating clinicians (e.g., with respect to treatment efficacy and best practices), internal auditing within the institution, quality assurance, etc.

Historically, each patient's medical record was maintained as a physical paper folder, often referred to as a "medical chart," or "chart." Each patient's chart would include a stack of paper reports, such as intake forms, medical history and immunization records, laboratory results, and/or clinicians' notes. Following an encounter with the patient (e.g., an office visit, a hospital round, or a surgical procedure), a clinician conducting the encounter would provide a narrative note about the encounter to be included in the patient's chart. Such a note may include, for example, a description of the reason(s) for the patient encounter, an account of any vital signs, test results, and/or other clinical data collected during the encounter, one or more diagnoses determined by the clinician from the encounter, and/or a description of a plan for further treatment.

Medical professionals other than clinicians may also provide narrative notes to be included in patients' charts. For example, a radiologist may analyze information obtained from an imaging study and generate a medical report that includes the radiologist's impressions. Such impressions may include, for example, the radiologist's interpretations of one or more medical images (e.g., one or more diagnoses) and/or notes for possible follow-up tests, procedures, and/or treatments.

Often, a medical professional would dictate a note into an audio recording device or a telephone giving access to such a recording device, to spare the medical professional the time it would take to prepare the note in written form. Later, a medical transcriptionist would listen to the audio recording and transcribe it into text, which could be inserted on a piece of paper into the patient's chart for later reference.

Currently, many healthcare institutions are transitioning or have transitioned from paper documentation to electronic medical record systems, in which patients' longitudinal medical information is stored in a data repository in electronic form. Besides the significant physical space savings afforded by the replacement of paper record-keeping with electronic storage methods, the use of electronic medical records provides beneficial time savings and other opportunities to clinicians and other healthcare personnel. For example, when updating a patient's electronic medical record to reflect a current patient encounter, a clinician need only document the new information obtained from the encounter, and need not spend time entering unchanged information such as the patient's date of birth, gender, medical history, etc. Electronic medical records can also be shared, accessed, and updated by multiple different persons locally and from remote locations through suitable user interfaces and network connections, eliminating the need to retrieve and deliver paper files from a crowded file room.

SUMMARY

In accordance with some embodiments, a system is provided, comprising at least one processor and at least one storage medium storing executable instructions, the at least one processor being programmed by the executable instructions to: use at least one natural language understanding engine to analyze at least one narrative provided by a radiologist in connection with a study of one or more medical images; apply one or more decision rules to one or more facts extracted by the at least one natural language understanding engine from the at least one narrative; and provide guidance to the radiologist based at least in part on a result of applying the one or more decision rules to the one or more facts extracted from the at least one narrative.

In accordance with some embodiments, a method is provided, comprising acts of: using at least one natural language understanding engine to analyze at least one narrative provided by a radiologist in connection with a study of one or more medical images; using at least one processor to apply one or more decision rules to one or more facts extracted by the at least one natural language understanding engine from the at least one narrative; and providing guidance to the radiologist based at least in part on a result of applying the one or more decision rules to the one or more facts extracted from the at least one narrative.

In accordance with some embodiments, at least one computer-readable storage medium is provided, having stored thereon instructions that, when executed by at least one processor, perform a method comprising acts of: using at least one natural language understanding engine to analyze at least one narrative provided by a radiologist in connection with a study of one or more medical images; applying one or more decision rules to one or more facts extracted by the at least one natural language understanding engine from the at least one narrative; and providing guidance to the radiologist based at least in part on a result of applying the one or more decision rules to the one or more facts extracted from the at least one narrative.

BRIEF DESCRIPTION OF DRAWINGS

In the drawings:

FIG. 7 shows an illustrative decision rule 700 written in an XML format, in accordance with some embodiments;

FIG. 9 FIG. 9 shows an illustrative medical report 900 that may be analyzed using a QA tool to provide guidance to a medical professional, in accordance with some embodiments;

FIG. 10 shows an illustrative user interface 1000 for creating and/or reviewing medical reports, in accordance with some embodiments.

DETAILED DESCRIPTION

Figure 1:
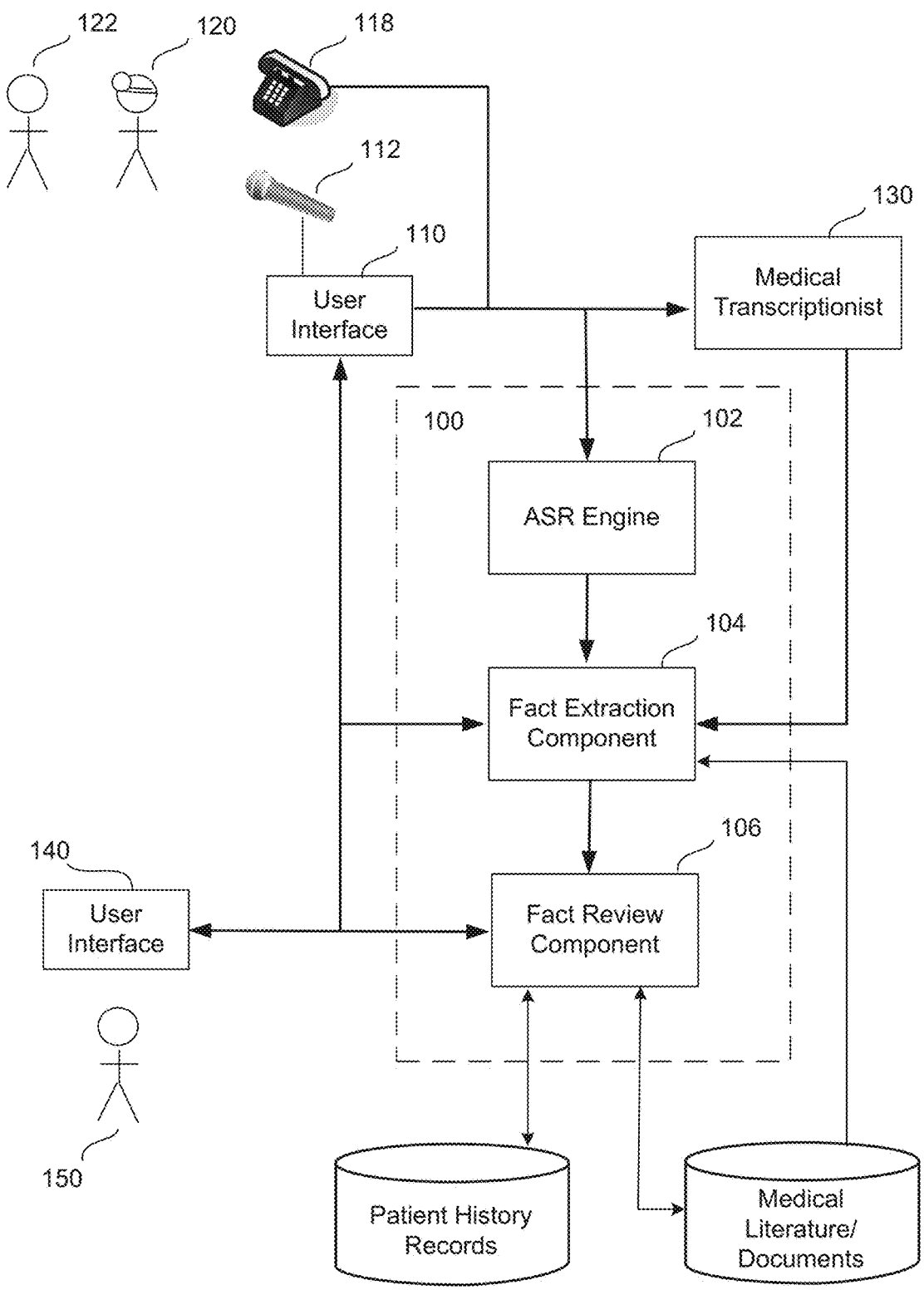
FIG. 1 shows an illustrative operating environment for a medical fact extraction system, in accordance with some embodiments.

In some embodiments, an Electronic Health Record (EHR) contains data documenting the care that a patient receives over time. Generally, although not required, an EHR is maintained by a healthcare institution and documents the care the patient receives from that institution. In some embodiments, an EHR is maintained as a structured data representation, such as a database with structured fields, although not all embodiments are limited in this respect. Each piece of information stored in such an EHR may be represented as a discrete (e.g., separate) data item occupying a field of the EHR database. For example, a 55-year-old male patient named John Doe may have an EHR database record with "John Doe" stored in the patient_name field, "55" stored in the patient_age field, and "Male" stored in the patient_gender field. Data items or fields in such an EHR are structured in the sense that only a certain limited set of valid inputs is allowed for each field. For example, the patient_name field may require an alphabetic string as input, and may have a maximum length limit; the patient_age field may require a string of three numerals, and the leading numeral may have to be "0" or "1;" the patient_gender field may only allow one of two inputs, "Male" and "Female;" a patient_birth_date field may require input in a "MM/DD/YYYY" format; etc.

In some embodiments, EHR content may be subject to one or more vocabulary constraints. For instance, medical terms may be normalized to a standard set of terms used by an institution or organization maintaining an EHR. The standard set of terms may be specific to the institution, or may be a more widely used standard. For example, a medical professional dictating or writing a free-form note may use any of a number of different terms (e.g., "heart attack," "acute myocardial infarction," "acute MI," and "AMI") to refer to the same condition suffered by a patient (e.g., an interruption of blood supply to the heart). To facilitate sharing of EHR data between various departments and users, and/or recognizing identical conditions across different patient records for data analysis, each individual medical concept may be represented using only one standardized term in an EHR. For example, "acute myocardial infarction" may be selected as the standard term for use in all EHRs maintained by an institution to denote a heart attack. In some embodiments, medical concepts may be represented in EHRs using a data format associated with a coding standard, such as the International Classification of Disease (ICD) standard. For example, "acute myocardial infarction" may be represented in an EHR as "ICD-9 410", where 410 is the code number for "acute myocardial infarction" according to the ninth edition of the ICD standard.

In some embodiments, EHRs are accessed through user interfaces that make extensive use of point-and-click input methods to allow clinicians and other healthcare personnel to enter medical documentation data directly into an EHR in its discrete structured data format. While some data items, such as the patient's name, may require input in alphanumeric form, many data items can be input simply through the use of a mouse or other pointing input device (e.g., a touch screen) to make selections from pre-set options (e.g., through drop-down menus, checkboxes, radio buttons, etc.).

However, many medical professionals may prefer to enter medical data by providing a free-form note, rather than using a data-entry interface that requires a user to navigate through different screens, menus, text fields, checkboxes, radio buttons, etc. Medical professionals may also prefer to use medical terms of their own choice, as opposed to being confined to a set of standard terms (e.g., as imposed by a certain organization or institution).

Moreover, medical professionals may prefer to dictate a note because speaking can often be faster than typing. For instance, dictation allows a radiologist to provide his impressions as he is viewing one or more medical images, without having to switch his visual attention to another physical or virtual screen to type or click. A dictated note may be transcribed into text by a human transcriptionist or by an Automatic Speech Recognition (ASR) engine.

Whether by speaking or typing, free-form narration allows medical professionals to be unconstrained in what they say and how they say it. Accordingly, some embodiments described herein relate to techniques for enhancing the creation and processing of electronic medical records from free-form notes. For example, some embodiments involve automatically extracting medical facts from free-form narration, which may be performed using one or more natural language understanding techniques such as entity detection. Entity detection involves the processing of text to identify mentions of particular things (entities) of interest (e.g., medical facts), despite variations in the terms people use to express those things. Examples of entity detection techniques are discussed in greater detail below.

The use of automatic fact extraction may allow medical professionals to provide free-form input, while retaining the advantages of storing, processing, maintaining, and accessing medical documentation data electronically. For example, the availability of a patient's medical documentation data as a collection of discrete structured data items may facilitate efficient queries for individual data items of interest and/or automatic assembly of a desired subset of the patient's data items into new reports, orders, invoices, etc.

The inventor has recognized and appreciated new ways to exploit the ability to extract medical facts from free-form input. For example, in some embodiments, a medical professional may provide free-form input in connection with an examination or study of a patient, and one or more medical facts extracted from the free-form input may be analyzed automatically to provide guidance to the medical professional (or a different medical professional) with respect to the care of the patient.

The inventor has recognized and appreciated that, although guidelines have been developed in many medical fields to assist medical professionals in various aspects of their practices (e.g., diagnosis, treatment, reporting, etc.), such guidelines may not be always followed. For example, some medical professionals may not be aware of the most up-to-date guidelines, or may choose not to follow such guidelines. Furthermore, guidelines may come from multiple different sources, such as journals (which may or may not be peer reviewed), regulatory agencies (e.g., international, federal, state, and local agencies), professional organizations, hospitals, departments within a hospital, insurance companies, etc. It may be burdensome for a medical professional to collect all relevant guidelines and maintain them in a way that is easily accessible. Further still, even if a medical professional is diligent in collecting and maintaining copies of guidelines, he may not always recognize that a particular guideline is applicable in a given situation and as a result may fail to look up and follow that guideline. Further still, it may be time consuming for a medical professional to look up a particular guideline (e.g., from an electronic or paper copy of a journal article). Therefore, the medical professional may be inclined to rely on his memory, rather than actually looking up the guideline. This may increase the risk that the medical professional misapplies the guideline.

The inventor has recognized and appreciated that following guidelines incorrectly, or failing to follow guidelines, may negatively impact medical practices. For example, a medical professional and/or an affiliated institution may be liable for adverse health consequences suffered by a patient if such consequences could have been avoided had the medical professional correctly followed the relevant guidelines for diagnosis, treatment, etc.

As another example, the failure to follow reporting guidelines may lead to insurance claims being rejected and payments being delayed.

Accordingly, the inventor has recognized and appreciated that it may be beneficial to automatically provide guidance to a medical professional to facilitate compliance with one or more guidelines. In some embodiments, a free-form note provided by a medical professional may be analyzed automatically to verify compliance with one or more guidelines, for example, by automatically extracting one or more medical facts from the free-form note and applying one or more decision rules to the extracted facts and/or other available information. Non-limiting examples of decision rules include rules to check whether certain guidelines are applicable in the given situation, rules to check whether the medical professional provided all of the information called for by certain reporting guidelines, rules to check whether one or more findings and/or recommendations made by the medical professional are correct under certain medical guidelines, rules to check whether the medical professional neglected to make a finding or recommendation that is warranted under certain medical guidelines, etc. Other types of decision rules may also be used, as aspects of the present disclosure are not limited to the use of any specific type of decision rules.

In some embodiments, medical reports may be analyzed in real time to provide feedback to medical professionals in a timely manner. For example, a free-form note provided by a medical professional regarding an examination or study of the patient may be analyzed before the medical professional "signs off" on the report. In this manner, if a problem is identified (e.g., a missing item of information, an incomplete or incorrect recommendation, etc.), one or more alerts may be generated and the medical professional may be prompted to correct and/or supplement the report. The inventor has recognized and appreciated that identifying problems in real time may improve efficiency because the medical professional may still remember details relating to the report and/or have easy access to relevant information. For example, in the case of a radiology report, the radiologist may still have the relevant images on his screen and be able to review the images when correcting and/or supplementing the report. However, it should be appreciated that aspects of the present disclosure are not limited to real-time analysis of medical reports, as such analysis may alternatively be done after the reports have been finalized and submitted.

As used herein, a "report" may include any suitable type or types of content. For example, a report may include a free-form note dictated, typed, handwritten, or otherwise provided by a medical professional. Additionally, or alternatively, a report may include one or more discrete items of information provided by a medical professional via a suitable data entry interface (e.g., a point-and-click interface). Furthermore, a "report" may be at any stage of preparation. For example, an initial report may include raw text and/or discrete information items provided by a medical professional. As another example, an intermediate report may be created, for instance, by augmenting an initial report with newly obtained information (e.g., one or more facts extracted from raw text in the initial report, information retrieved from relevant patient records, etc.). As another example, a final report may be created by incorporating changes requested by a medical professional after reviewing a draft report, and may be formatted according to one or more applicable formatting rules.

The inventor has recognized and appreciated that it may be beneficial to develop decision rules based on medical guidelines from authoritative sources such as professional organizations, peer-reviewed journal articles, etc. Such guidelines may be developed by well-respected scholars and/or practitioners based on rigorous research and/or clinical studies. As a result, medical professionals may be more receptive to following such guidelines. Accordingly, in some embodiments, an alert provided to a medical professional regarding a potential problem in a medical report may be accompanied by an identification of one or more guidelines used to identify the potential problem. This may assist the medical professional in determining whether to follow the guideline, ignore the alert, or seek further information before making a decision.

As discussed above, the inventor has recognized and appreciated that it may be burdensome for a medical professional to create and maintain a comprehensive and up-to-date collection of guidelines. Accordingly, in some embodiments, a collection of decision rules may be updated (e.g., with decision rules added, deleted, or modified) on an ongoing basis, for example, whenever new or modified guidelines become available. In some embodiments, a guideline management system may monitor one or more potential sources of guidelines (e.g., one or more government agencies, professional organizations, journals, etc.), for example, by receiving notifications from such sources and/or performing scheduled searches at any suitable frequency. When new guidelines and/or changes to existing guidelines are detected, the collection of rules may be updated accordingly. In this manner, medical professionals can have confidence that a comprehensive and up-to-date collection of guidelines is being followed, without having to create and maintain such a collection themselves.

In some embodiments, decision rules may be written in a standard format (e.g., an XML format) and may be provided as input to a decision engine that is configured to parse and apply such rules. In this manner, decision rules may be easily customized, for example, for different medical disciplines (e.g., general practice vs. radiology), different regulatory jurisdictions (e.g., countries, states, etc.), different hospitals, etc. The customized rules may be stored as different rule sets in any suitable manner, such as in a database that allows efficient searching and retrieval. Additionally, by separating the decision rules from the decision engine, the decision rules may be updated without having to modify the decision engine. However, not all embodiments are limited to the use of a standard format for decision rules, nor to a decision engine that takes decision rules as input.

The inventor has recognized and appreciated that it may be beneficial to provide automatic assistance in report generation based on one or more guidelines. For example, as discussed above, a reporting guideline (e.g., as imposed by an insurance company) may call for certain pieces of information in a report. As another example, a follow-up guideline may call for knowledge of certain information before a definitive recommendation can be made. In some embodiments, a draft report may be automatically generated based on a free-form note provided by a medical professional and/or other available information, and the medical professional may be notified of one or more pieces of desired information that are still missing. Such notifications may be presented in any suitable manner, non-limiting examples of which are discussed below.

In some embodiments, in the event that a medical professional fails to provide a desired item of information, an assumed value may be automatically selected and presented to the medical professional for confirmation. The inventor has recognized and appreciated that automatically selecting and presenting assumed values may be more efficient than prompting the medical professional to explicitly provide the missing information. The efficiency gain may be significant where multiple pieces of information are to be solicited, because the medical professional may simply review the assumed values as part of the report review workflow, without being interrupted by a lengthy question-and-answer process.

Assumed values for missing information items may be selected in any suitable manner, as aspects of the present disclosure are not limited to any particular way of selecting assumed values. For example, if the missing item relates to the patient's demographic information or medical history, an assumed value may be looked up from the patient's health record. As another example, an assumption may be made based on what is known about the patient in conjunction with statistical observations from a relevant population. For instance, in some embodiments, if a radiologist preparing a report regarding a pulmonary nodule did not indicate whether the patient is a smoker or non-smoker, an assumption may be made that the patient is a non-smoker because it is known that the patient is a 65-year-old female and it is further known that a female aged between 50 and 60 is more likely to be a non-smoker than a smoker.

In some embodiments, one or more decision rules may be applied based on one or more assumed values. In the event that the medical professional identifies an incorrect assumption, some or all of the decision rules may be reapplied dynamically based on one or more corrections provided by the medical professional. For example, some or all of the decision rules may be reapplied automatically in response to the medical professional identifying and correcting an incorrect assumption, and a corrected draft report may be automatically generated. In some embodiments, changes to the draft report may be highlighted in a suitable manner to facilitate review by the medical professional.

While a number of inventive techniques are described herein for creating and/or processing medical reports, it should be appreciated that embodiments of the present disclosure may include any one of these techniques, any combination of two or more techniques, or all of the techniques, as aspects of the present disclosure are not limited to the use of any particular number or combination of the techniques described herein. The aspects of the present disclosure described herein can be implemented in any of numerous ways, and are not limited to any particular implementation. Described below are examples of specific implementations; however, it should be appreciate that these examples are provided merely for purposes of illustration, and that other implementations are possible.

Figure 2:
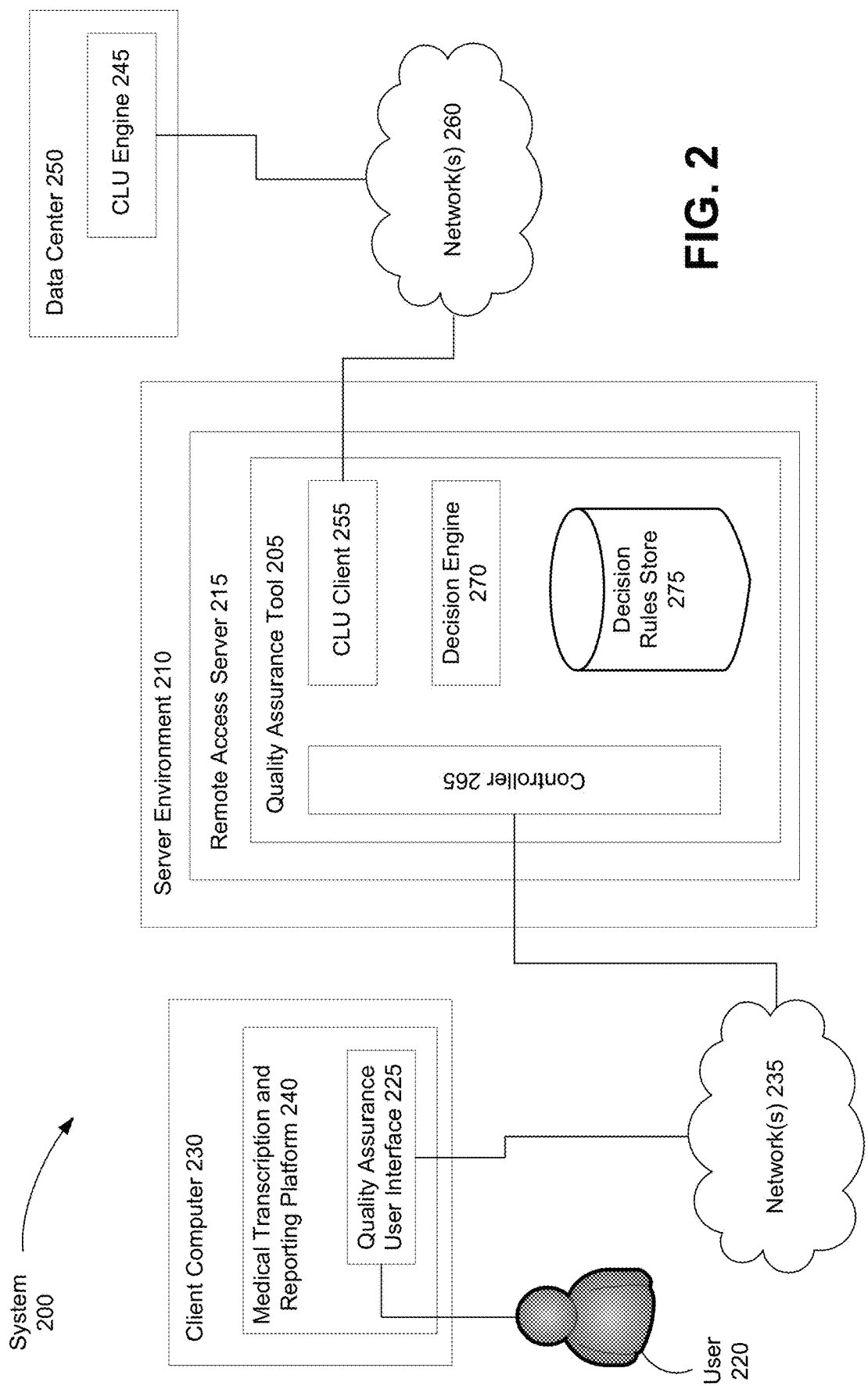
FIG. 2 shows an illustrative system 200 in which a quality assurance (QA) tool for processing medical reports may be used, in accordance with some embodiments.

One illustrative application of the techniques described herein is a quality assurance (QA) tool for use in processing medical reports. FIG. 2 shows an illustrative system 200 in which such a QA tool may be used, in accordance with some embodiments. In this example, the system 200 includes multiple computers configured to communicate with each other via one or more networks. It should be appreciated that such an arrangement is merely illustrative, as other arrangements may also be suitable. For example, all of the functionalities described herein in connection with the system 200 may be implemented on a single computer, as opposed to being distributed over multiple computers. Furthermore, the processing tasks described herein may be distributed over multiple computers in any suitable way, as aspects of the present disclosure are not limited to any particular distribution of processing tasks.

In the example of FIG. 2, a QA tool 205 is implemented as a process that is running in a server environment 210 and can be accessed through a remote access server 215. The remote access server 215 may handle various tasks (e.g., authentication) to allow a user 220 to access the QA tool 205 from a QA user interface 225. The remote access server 215 may use any suitable remote access protocol or combination of such protocols, as aspects of the present disclosure are not limited to any particular way of accessing the QA tool 205.

In the example of FIG. 2, the QA user interface 225 runs on a client computer 230 that is located remotely from the server environment 210 and is configured to communicate with the server environment 210 through one or more networks 235. However, it should be appreciated that in alternative embodiments the QA user interface 225 may run on a computer that is on the same local area network as the server environment 210, or may run on the same hardware as the server environment 210.

In some embodiments, the QA tool 205 may be provided to the user 220 as part of a bundle of capabilities related to creating and processing medical reports. For example, an automatic transcription service (not shown) may be provided to perform automatic speech recognition (ASR) processing on audio signals captured from the user 220. This may allow the user 220 to dictate a medical report or one or more portions thereof and then submit the transcribed text to the QA tool 205 for further processing, such as verification of compliance with one or more guidelines. However, it should be appreciated that aspects of the present disclosure are not limited to the use of ASR in creating medical reports. A report may be generated in any suitable way, such as by typing, pointing-and-clicking, and/or handwriting (e.g., via automatic handwriting recognition).

In some embodiments, the QA tool 205 may be integrated with one or more other processes related to creating and processing medical reports (e.g., automatic transcription) to provide a seamless user experience. This may be accomplished by providing access to these processes via a single platform, such as the illustrative medical transcription and reporting platform 240 shown in FIG. 2. However, it should be appreciated that aspects of the present disclosure are not limited to the use of a unified platform, as the QA tool 205 may alternatively be provided as a stand-alone process.

As discussed above, in accordance with some embodiments, one or more NLU techniques may be used to process medical reports (e.g., to extract one or more facts from a medical report). Again, the techniques described herein may be applied to any suitable types of medical reports, including finished reports ready to be included in patient medical records and/or reports that are still works in progress.

Accordingly, in some embodiments, the QA tool 205 may invoke a NLU engine to process the medical reports to be quality assured. The NLU engine may be built and/or tuned using information specific to the medical field. Non-limiting examples of such information include a lexicon of medical terms, an ontology linked to medical terms, a medical knowledge representation model, a statistical entity detection model trained using hand-annotated medical documents, and/or a statistical relation model similarly trained. Such an NLU engine is sometimes referred to herein as a clinical language understanding (CLU) engine. Various illustrative ways to implement a CLU engine are described in greater detail below.

Although expert knowledge in the medical field may enhance the system's ability to extract facts from medical reports, it should be appreciated that not every component of a CLU engine may incorporate such knowledge. In various embodiments, one or more components of a CLU engine may be generic (i.e., not specific to medicine). On the other hand, one or more components of a CLU engine may incorporate knowledge from one or more subfields within the medical field (e.g., radiology). Thus, a CLU engine may be built and/or tuned using domain knowledge at any suitable level of specificity, as aspects of the present disclosure are not limited to any particular way of building and/or tuning a CLU engine.

In the example shown in FIG. 2, the QA tool 205 uses a CLU engine 245 to extract facts from medical reports. In this embodiment, the CLU engine 245 is implemented as a process running at a data center 250, which may be a cloud computing facility or some other type of facility that is capable of performing computational tasks associated with the CLU engine 245. The QA tool 205 may use a CLU client 255 to access the CLU engine 245 via one or more networks 260.

In some embodiments, the QA tool 205 may operate in real time. For example, in some embodiments, the QA tool 205 may check a medical report as soon as the report text becomes available and/or before the author "signs" the report. In an embodiment in which an ASR engine is used to convert a medical professional's speech into text, the QA tool 205 may check the report text as soon as it is output by the ASR engine. However, it should be appreciated that aspects of the present disclosure are not limited to the use of an ASR engine, as medical reports may be prepared in other ways, such as by typing, handwriting, etc.

As used herein, "signing" is an act performed by an author of a report (e.g., a clinician or lab technician) to indicate the report is ready to be made part of a patient's medical record. Depending on the particular implementation, this act may or may not include the author attaching an electronic signature to the report, and the electronic signature may or may not be a cryptographic signature. Furthermore, the author may sign the report before the report is complete, and may supplement the report with additional information at a later time.

While the CLU engine 245 runs at a data center in some embodiments, such an arrangement is not required. The CLU engine 245 may in alternative embodiments execute within the server environment 210 or on the client computer 230. Also, the QA tool 205 need not operate in real time. For example, in alternative embodiments, the QA tool 205 may process medical reports offline (e.g., in batches).

In some embodiments, the QA tool 205 may receive the report text to be processed from the client computer 230. For example, the QA tool 205 may receive the report text from the QA user interface 225 or some other component of the medical transcription and reporting platform 240. In an embodiment in which an ASR engine (not shown) is used to transcribe a dictated note into text, the QA tool 205 may receive the report text directly from the ASR engine, which may run on the client computer 230 or some other computer (e.g., a remote server computer).

In the example shown in FIG. 2, a controller component 265 of the QA tool 205 may interact with the QA user interface 225 to receive medical reports to be processed and/or to return processing results. Upon receiving a medical report from the QA user interface 225 or some other source, the controller 265 may obtain certain data from the report, such as the text to be checked and/or any desired combination of metadata that may be used to inform the CLU engine's analysis. Non-limiting examples of metadata include patient gender, order procedure code (e.g., as established by a medical institution, insurance company, government agency, or other organization), order procedure description (e.g., "XRAY Left Leg"), etc. The data may then be passed to the CLU client 255 to be submitted to the CLU engine 245 for analysis.

In some embodiments, the CLU client 255 may forward some or all of the output received from the CLU engine 245 to a decision engine 270 of the QA Tool 205 for further processing. In alternative embodiments, the CLU client 255 may forward the CLU engine output to the controller 265, which may in turn forward some or all of the CLU engine output to the decision engine 270. The controller 265 may, although need not, perform some intermediate processing on the CLU engine output, such as converting the CLU engine output to a format expected by the decision engine 270 and/or supplementing the CLU engine output with other available information. However, it should be appreciated that these data paths are provided solely for purposes of illustration, as aspects of the present disclosure are not limited to any particular manner of conveying data between different system components.

In some embodiments, the decision engine 270 and/or the controller 265 may be programmed to parse the output of the CLU engine 245, which may be in any suitable format (e.g., an XML format such as a Clinical Document Architecture (CDA) format), and identify one or more facts extracted by the CLU engine 245 from the input medical report. The decision engine 270 may analyze the extracted facts to provide guidance with respect to the care of the patient to whom the input medical report pertains. For example, in some embodiments, the decision engine 270 may use the extracted facts to identify one or more guidelines that are applicable to the input medical report and/or verify whether the input medical report complies with one or more guidelines.

The decision engine 270 may verify the input medical report against any suitable guideline or combination of guidelines. In some embodiments, a guideline may specify one or more desired items of information for a given type of medical report. For example, a guideline may specify that a radiologist indicate in a radiology report one or more of: patient age, patient gender (e.g., male, female, or unknown), type of study conducted (e.g., a chest computed tomography (CT) scan), findings, impressions, etc. As another example, a guideline may specify that, if a particular finding is present, the radiologist provide certain information that is considered relevant to that finding. For instances, in some embodiments, a guideline may specify that, if a pulmonary nodule is found in the study, the radiologist indicate one or more characteristics of the nodule, such as size, border (e.g., regular vs. irregular), morphology, etc. Other items of information may be specified instead of, or in addition to, the examples given above, as aspects of the present disclosure are not limited to any particular set of desired items of information.

An item of information may be specified for any suitable reason. For example, an insurance company may impose one or more reporting guidelines to ensure that a medical professional fully document the reasons for recommending a particular examination, study, treatment, procedure, follow-up, etc. If one or more specified items of information are missing from an insurance claim, the insurance company may be unable to determine whether the expenses incurred are justified and may deny the claim until all specified items of information have been furnished. As another example, a diagnostic guideline may call for one or more items of information to make a diagnosis. For instance, if a radiologist finds a pulmonary nodule, information from a prior study may be called for to confirm the nodule is benign (e.g., by confirming the nodule has not grown in size since the last study). If any specified information is unavailable, the guideline may specify an "indeterminate" diagnosis.

The inventor has recognized and appreciated that some guidelines may be published or otherwise made available in a form that is not conducive to efficient and accurate application. For example, a journal article or other type of publication may describe in a verbose manner how various sets of circumstances are mapped to respective recommendations and how the recommendations may be modified based on certain exceptions. It may be time consuming to read through such a publication to identify an appropriate recommendation based on what is known about a given patient. Accordingly, in some embodiments, decision rules are developed to encapsulate one or more guidelines provided in a publication. For example, in some embodiments, decision rules may be written in a standard format (e.g., an XML format) to facilitate automatic compliance verification.

In some embodiments, the illustrative decision engine 270 shown in FIG. 2 may be programmed to receive one or more decision rules as input and to parse and apply the one or more rules. For example, the decision engine 270 may be programmed to apply an input rule to a medical report to determine whether a guideline corresponding to the input rule is applicable to the medical report and/or to verify whether the medical report complies with the guideline. The decision engine 270 may apply input rules in any suitable manner, for example, by applying input rules to one or more facts extracted by the CLU engine 245 from the medical report and/or other information related to the medical report (e.g., information available from the medical record of a patient to whom the medical report pertains). The extracted facts and/or other information to which the input rules are applied may relate to any aspect of patient care, including, but not limited to the patient's demographic information, medical history, symptoms, treatment information, etc.

In some embodiments, if one or more decision rules are triggered, the decision engine 270 may generate one or more alerts accordingly. For example, the decision engine 270 may send alerts, either directly or via the controller 265, to the QA user interface 225 to be presented to the user 220 (e.g., visually, audibly, etc.). It should be appreciated that the user 220 may, although need not, be the author of the report that was verified by the QA tool 205. Illustrative examples of alerts and ways to present them are described below.

In some embodiments, one or more decision rules may be stored in a data store, such as the illustrative decision rules store 275 shown in FIG. 2. The decision rules store 275 may be organized in some suitable fashion, for example, to facilitate efficient searching and retrieval. In some embodiments, the decisional rules store 275 may be organized as a database that can be accessed using queries. Decision rules stored in such a database may be organized according to various attributes, such as medical discipline (e.g., general practice vs. radiology), regulatory jurisdiction (e.g., countries, states, etc.), hospital, etc. Relevant rules may be looked up by constructing a query that specifies one or more attribute values (e.g., all Massachusetts rules associated with radiology). In the example shown in FIG. 2, the decision engine 270 or some other component of the QA tool 205 (e.g., the controller 265) may be programmed to construct such a query based on information relating to a medical report being processed, such as information from the report text and/or any metadata associated with the report, information from a relevant patient medical record, and/or any other suitable information.

In some embodiments, the decision rules stored in the decision rules store 275 may be updated (e.g., with decision rules added, deleted, or modified) on an ongoing basis, for example, whenever new or modified guidelines become available. In some embodiments, the QA tool 205 or a separate guideline management system (not shown) may monitor one or more potential sources of guidelines (e.g., one or more government agencies, professional organizations, journals, etc.), for example, by receiving notifications from such sources and/or performing scheduled searches at any suitable frequency. When new guidelines and/or changes to existing guidelines are identified, one or more affected rules may be updated accordingly. In this manner, the decision rules stored in the decision rules store 275 may continue to reflect the most recent developments in various medical disciplines.

While some details of implementation are described above in connection with FIG. 2, it should be appreciated that such details are provided solely for purposes of illustration. The concepts described above may be implemented in other ways, for instance, without the use of the remote access server 215. For example, in alternative embodiments, the QA tool 205 may execute on a local computer, or may execute remotely and be accessed via a web interface. Furthermore, aspects of the present disclosure are not limited to the use of a CLU client for accessing a CLU engine, as the CLU engine may be invoked in any suitable way. Further still, the decision engine 270 may access decision rules from one or more remote data stores in addition to, or instead of, the decision rules store 275 shown in FIG. 2.

Figure 3:
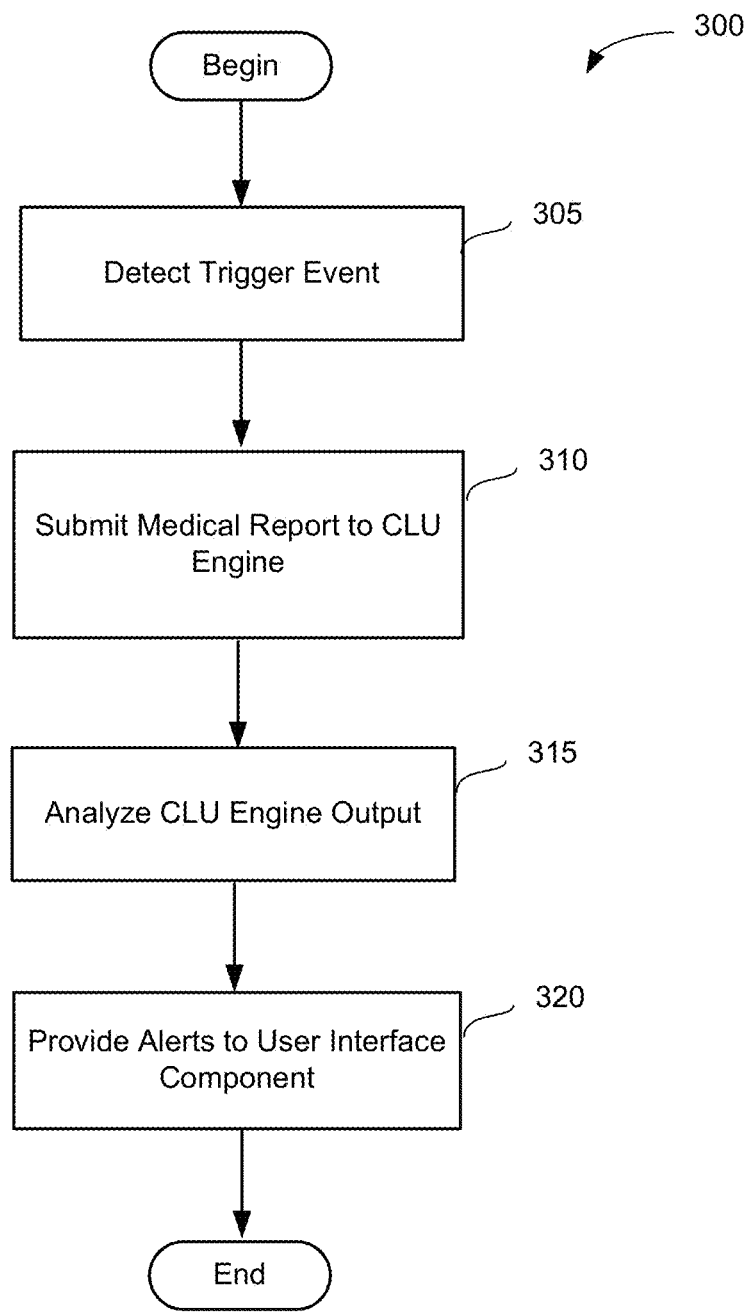
FIG. 3 shows an illustrative process 300 that may be performed to provide guidance to a medical professional, in accordance with some embodiments.

FIG. 3 shows an illustrative process 300 that may be performed to provide guidance to a medical professional, in accordance with some embodiments. For example, the process 300 may be performed by the illustrative QA tool 205 shown in FIG. 2 to facilitate compliance with one or more guidelines.

In the example shown in FIG. 3, a trigger event may be detected at act 305 to initiate quality assurance checks on one or more medical reports. Any suitable set of one or more events may be designated as trigger events. For example, in some embodiments, a user or system administrator may specify a set of one or more events so that an occurrence of any one event in the set may automatically trigger a quality assurance check. An example of a trigger event is an explicit request from the user to initiate quality assurance checking on one or more medical reports. Another example of a trigger event is an indication that the user is ready to "sign" or submit one or more medical reports. Another example of a trigger event is an indication that the user has completed an "IMPRESSION" section in a report (which may or may not be the last section of the report). For example, in an embodiment in which the user dictates the report, the user may say, "end of IMPRESSION section," "end of report," or a different section heading to indicate he is ready to work on a different section. This may result in one or more labels being inserted into the report to mark the end of the IMPRESSION section, which may in turn trigger a quality assurance check. Other types of trigger events may also be possible, as aspects of the present disclosure are not limited to any particular way of triggering a quality assurance check.

At act 310, one or more medical reports (or one or more portions thereof) to be quality assured may be submitted to a CLU engine for processing. The CLU engine may be configured to extract one or more facts from an input report using any one or combination of the techniques described herein. For example, in some embodiments, the CLU engine may be configured to extract positive findings (e.g., a finding that warrants immediate treatment, additional study, or at least follow-up at a later time). This may be done in any suitable manner, such as using a statistical fact extraction model trained on a corpus of hand-annotated medical reports, or some other technique that uses contextual information to identify positive findings.

In some embodiments, one or more pieces of metadata (e.g., patient gender, patient age, order procedure code, order procedure description, etc.) may be submitted to the CLU engine along with report text to supply additional contextual information. However, it should be appreciated that not all embodiments are limited to the use of metadata as contextual information in fact extraction. In some embodiments, the CLU engine may evaluate one or more portions of text in a medical report using, as contextual information, other text in the report.

At act 315 in the example of FIG. 3, one or more outputs of the CLU engine may be analyzed. As discussed above, an output of the CLU engine may be in any suitable format, non-limiting examples of which include markup language formats such as a Clinical Documentation Architecture (CDA) format or some other XML format. Accordingly, in some embodiments, analyzing an output of the CLU engine may include parsing the output according to parsing rules associated with the particular format expected from the CLU engine, for example, by identifying one or more sections in the document and searching those sections for one or more facts extracted by the CLU engine from the medical report.

In some embodiments, analyzing the output of the CLU engine may include applying one or more rules that perform functions in addition to parsing the CLU engine output. For example, as discussed above, one or more decision rules may be applied to one or more extracted facts in the CLU engine output and/or other information related to the medical report (e.g., information available from the medical record of a patient to whom the medical report pertains) to provide guidance in connection with diagnosis, treatment, reporting, etc.

In some embodiments, the application of rules may be done while parsing is still on-going. For example, when a particular section in the CLU engine output has been identified, an appropriate set of rules may be applied while the rest of the output is still being parsed. However, the application of rules may in alternative embodiments be performed after parsing has been completed. Also, it should be appreciated that applying a rule may also include searching the entire CLU engine output, without being limited to any particular portion of the output.

Depending on the particular implementation, decision rules may be selected in any suitable manner for application to a medical report. For example, in some embodiments, one or more rules (e.g., general reporting rules) may be applied to all medical reports. In some embodiments, one or more rules may be applied only to certain types of medical reports. For example, one or more rules may be applied only to reports relating to a particular medical discipline (e.g., cardiology, oncology, radiology, etc.). As another example, one or more rules may be applied only to reports generated for a particular hospital, a particular department or laboratory within a hospital, a particular user or group of users, etc. In some embodiments, one or more rules may be applied to classify a report, and one or more additional rules may be selected depending on the classification result. For example, if the report is classified as a CT report ordered by a physician from hospital X, one or more rules applicable to CT reports for hospital X may be retrieved (e.g., from a data store such as the decision rules store 275 in the example of FIG. 2) and applied to the report.

Returning to the example of FIG. 3, the application of one or more rules at act 315 may trigger one or more alerts. For example, an alert may be generated if it is determined that an item of information called for by at least one applicable guideline is missing from a report. As another example, an alert may be generated if it is determined that the report includes a recommendation that is inconsistent with at least one applicable guideline, or that a recommendation called for by at least one applicable guideline is missing from the report.

In some embodiments, an alert triggered at act 315 in the example of FIG. 3 may be provided to a user interface component (e.g., the illustrative QA user interface 225 shown in FIG. 2) at act 320 to be presented to the user (e.g., visually, audibly, etc.). The alert may be provided in any suitable manner. For example, in some embodiments, an explanation may be provided to assist the user in understanding the nature of the alert (e.g., missing information, incomplete and/or incorrect recommendation, etc.) Additionally, one or more pieces of information (e.g., facts extracted by the CLU engine, portions of report text, metadata, etc.) that triggered the alert may be provided to the user interface component, which may present the triggering information to the user in a manner that links the triggering information to the explanation of the alert.

In an embodiment in which certain specified item of information is missing from the report, an assumed value may be selected for the specified item of information and provided to the user interface component, which may prompt the user to review the selected value and provide any correction if necessary. In an embodiment in which an incomplete and/or incorrect recommendation is found in the report, an alternative recommendation may be provided to the user interface component for presentation to the user. The alternative recommendation may be accompanied by any suitable explanation (e.g., a list of one or more facts that formed the basis for the alternative recommendation), or no explanation at all.

In some embodiments, an alert may be provided to the user interface component along with an identification of one or more guidelines corresponding to the rule that triggered the alert. As discussed above, this information may assist the user in determining how to respond to the alert (e.g., adopting the alternative recommendation provided in the alert, ignoring the alert, seeking additional information, etc.).

Although various examples of alert information are described herein, it should be appreciated that aspects of the present disclosure are not limited to any such example. Any suitable type of information may be provided to the user interface component for presentation to the user. Furthermore, the user interface component may present alerts to the user in any suitable manner, examples of which are discussed in greater detail below.

Figure 4:
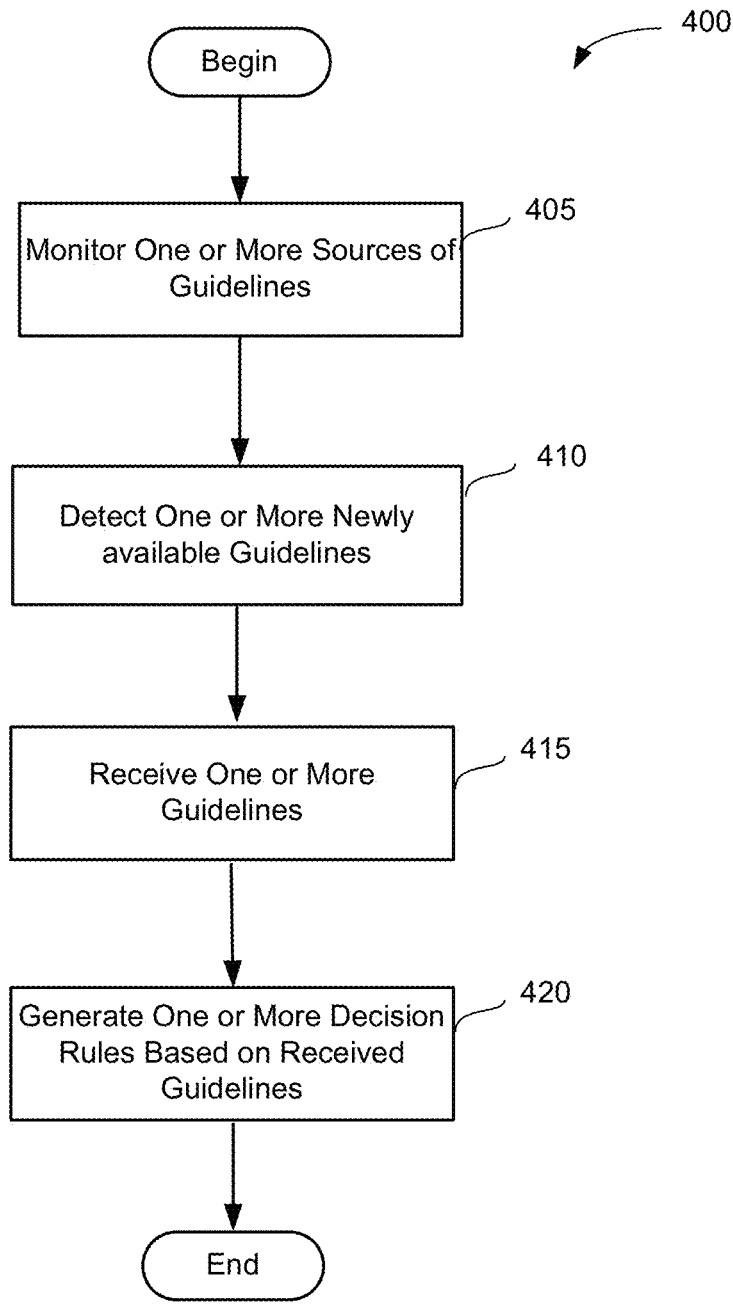
FIG. 4 shows an illustrative process 400 that may be performed to create and/or maintain a collection of decision rules, in accordance with some embodiments.

FIG. 4 shows an illustrative process 400 that may be performed to create and/or maintain a collection of decision rules, in accordance with some embodiments. For example, the process 400 may be performed by the illustrative QA tool 205 shown in FIG. 2 or a separate guideline management system to facilitate compliance with a comprehensive and up-to-date collection of guidelines.

At act 405, one or more potential sources of guidelines may be monitored. Non-limiting examples of sources of guidelines include government agencies, professional organizations, peer-reviewed journals, etc. These sources may develop and/or endorse the guidelines. Alternatively, or additionally, other sources of guidelines may be monitored that simply collect and make available published guidelines without being responsible for their content.

The monitoring of guideline sources may be done in any suitable manner. In some embodiments, notifications of newly available guidelines may be received via a subscription to a source of guidelines (which may be paid or unpaid). In some embodiments, searches for newly available guidelines may be performed via an interface (e.g., a web interface to a guideline database) provided by a source of guidelines. The searches may be performed according to a schedule (e.g., periodically at any suitable frequency, such as daily, weekly, monthly, bimonthly, quarterly, semiannually, annually, etc.), or may be triggered manually by a user at any suitable time (e.g., when at least some report text is available).

At act 410, one or more newly available guidelines may be detected as a result of the monitoring performed at act 405. The newly available guidelines may include new guidelines and/or modifications to existing guidelines. At act 415, one or more guidelines may be received, which may include the newly available guidelines. For example, in some embodiments, in response to detecting the newly available guidelines at act 410, a request may be sent automatically to an appropriate guideline source and the newly available guidelines may be received as a result of the request.

At act 420, one or more decision rules may be generated based at least in part on the one or more guidelines received at act 415. For example, one or more new decision rules may be created to reflect a new guideline, and/or one or more existing decision rules may be modified to reflect a change in an existing guideline. In some embodiments, creating a decision rule for a guideline may include identifying one or more decisions to be made based on available information and one or more recommendations called for by the guideline based on the outcomes of the one or more decisions. Similarly, modifying a decision rule may include identifying a change in a decision to be made and/or a recommendation called for by the guideline. An example of a guideline and a corresponding decision rule are described in detail below in connection with FIGS. 5-6.

It should be appreciated that the illustrative process 400 shown in FIG. 4 and described above is merely one example of a process that may be performed to create and/or maintain a collection of decision rules. Decision rules may be created and/or maintained in other ways, as aspects of the present disclosure are not limited in this respect. For example, a decision rule may be deleted from a collection of decision rules when the corresponding guideline becomes out of date. As another example, instead of a guideline management system "pulling" newly available guidelines from a source, such guidelines may be "pushed" to the guideline management system by the source. For instance, in some embodiments, the guideline management system may simply wait for a source to distribute up-to-date guidelines, rather than actively monitoring the source.

Figure 5:
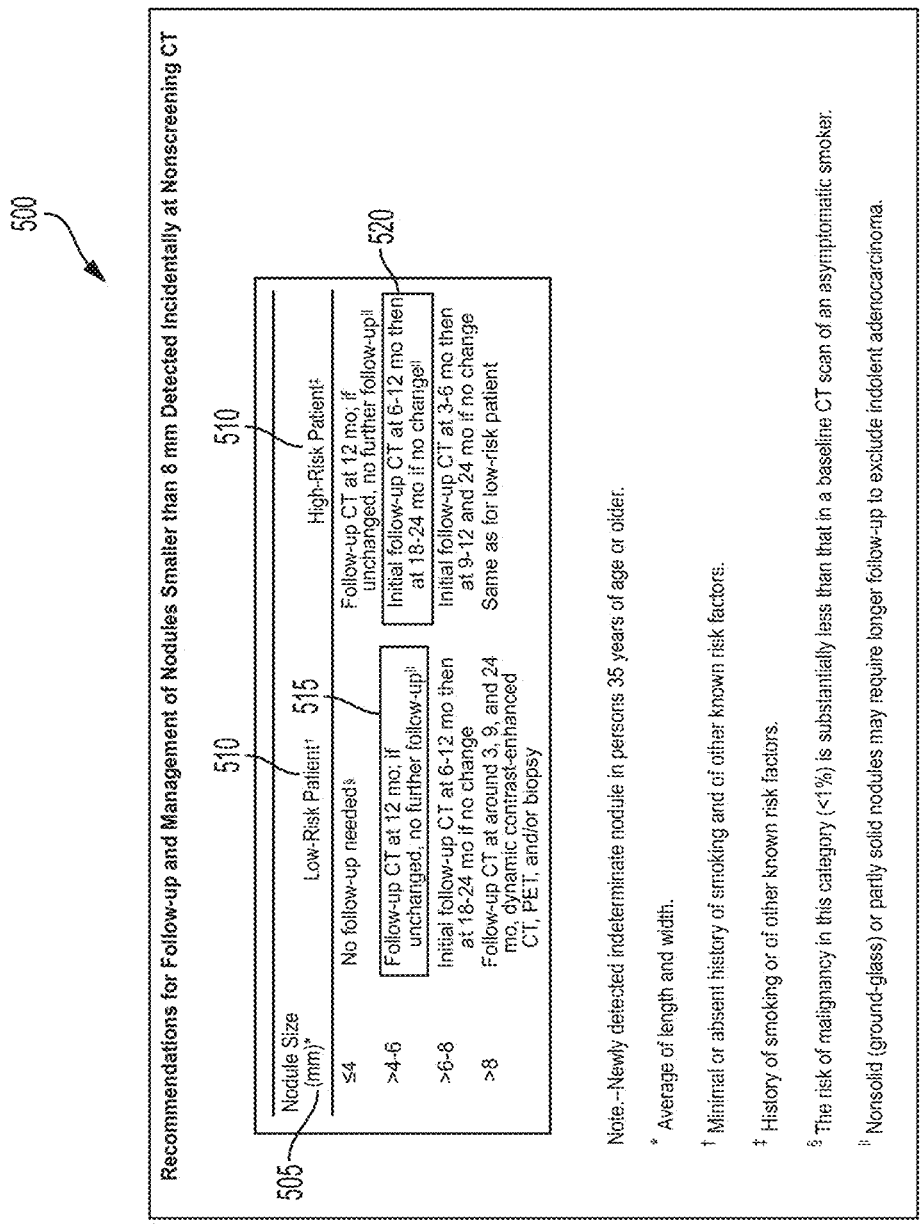
FIG. 5 shows an illustrative guideline 500 that may be used to generate one or more decision rules, in accordance with some embodiments.

FIG. 5 shows an illustrative guideline 500 that may be used to generate one or more decision rules, in accordance with some embodiments. In this example, the guideline 500 is the Fleischner Society's recommendations for the follow-up and management of small pulmonary nodules detected incidentally at non-screening CT scans. The guideline 500 appeared in an article in the *Radiology* journal published by the Radiology Society of North America, Inc. (MacMahon, H., et al., *Guidelines for Management of Small Pulmonary Nodules Detected on CT Scans: A Statement from the Fleischner Society, Radiology,* 237:395-400, November 2005.)

In the example of FIG. 5, the guideline 500 calls for two items of information: nodule size (shown at 505) and patient risk category (shown at 510). Different follow-up procedures may be recommended based on how large the nodule is (e.g., 4 mm or less, between 4 mm and 6 mm, between 6 mm and 8 mm, or greater than 8 mm) and/or whether the patient is low risk or high risk. For example, as shown at 515, if the nodule size is between 4 mm and 6 mm and the patient is low risk, the guideline 500 calls for follow-up CT in 12 months and no further follow-up if the nodule size is unchanged. If, however, the patient is high risk (as shown at 525), the guideline 500 calls for an initial follow-up CT in 6-12 months and another follow-up CT in 18-24 months if the nodule size is unchanged.

Figure 6:
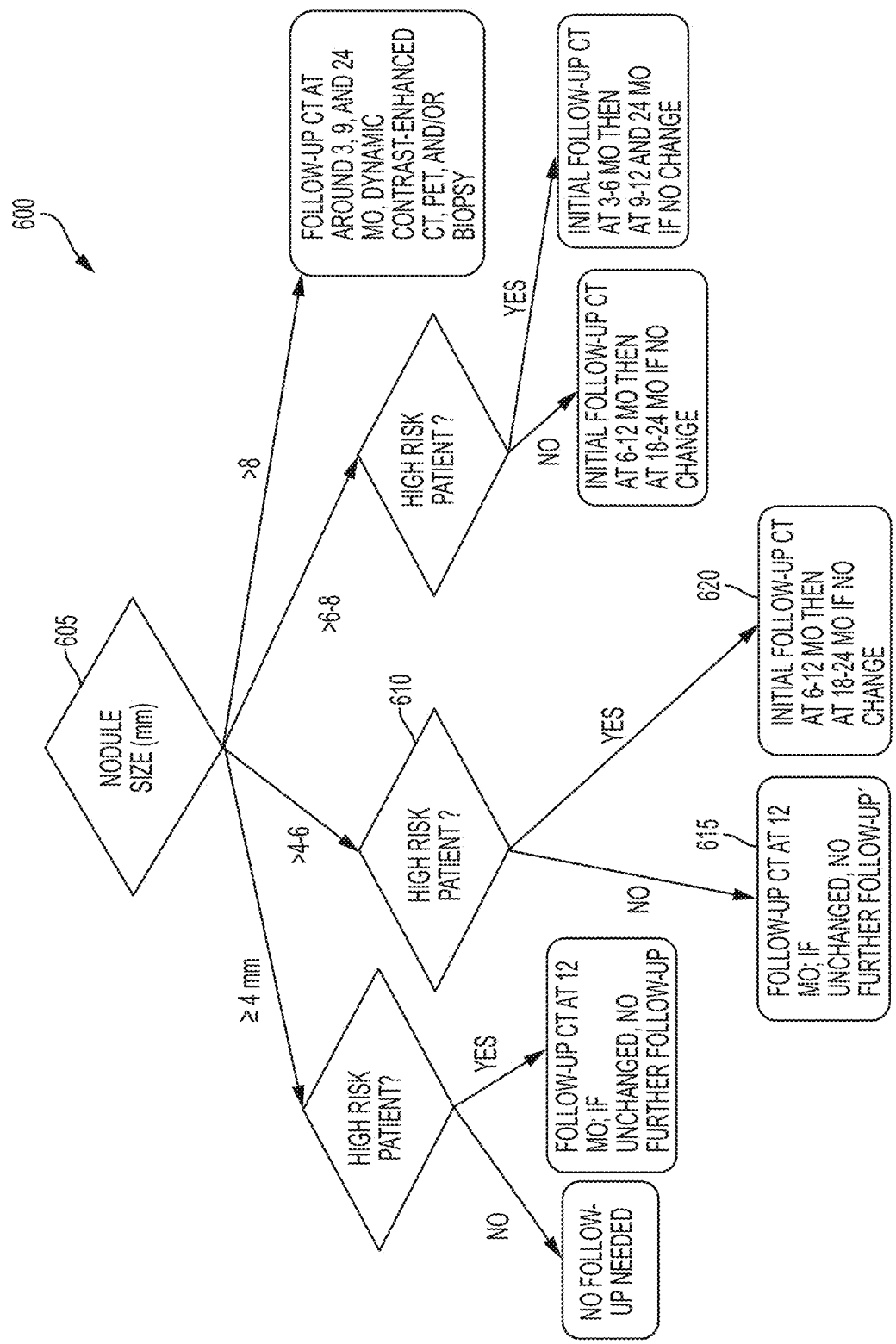
FIG. 6 shows an illustrative decision tree 600 that may be constructed to represent the illustrative guideline 500 in the example of FIG. 5, in accordance with some embodiments.

FIG. 6 shows an illustrative decision tree 600 that may be constructed to represent the guideline 500 in the example of FIG. 5, in accordance with some embodiments. In this example, the decision tree 600 has two levels of internal nodes, corresponding respectively to the two decisions to be made with respect to nodule size and patient risk category. Starting at the root node 605, it is determined which of the four ranges (i.e., 4 mm or less, between 4 mm and 6 mm, between 6 mm and 8 mm, or greater than 8 mm) the nodule size falls into. If, for example, the nodule size is between 4 mm and 6 mm, then it is determined at the internal node 610 whether the patient is low risk or high risk. This risk determination leads to either one of two leaf nodes, 615 and 620. If the patient is low risk, then the "No" branch is followed, leading to the leaf node 615 with the recommendation of follow-up CT in 12 months and no further follow-up if the nodule size is unchanged. If, on the other hand, the patient is high risk, then the "Yes" branch is followed, leading to the leaf node 620 with the recommendation of an initial follow-up CT in 6-12 months and another follow-up CT in 18-24 months if the nodule size is unchanged.

Thus, in some embodiments, a decision tree may be a tree in which every internal node (including the root node) corresponds to a decision, and a path through the tree may lead to a leaf node that corresponds to a recommendation. A decision may be binary (e.g., a yes/no condition such as whether the patient is high risk), or may have more than two possible outcomes (e.g., four possible ranges for nodule size). Furthermore, the decision may be made based on any suitable information. For instance, although in the example of FIG. 5 each decision is made on the basis of a single item of information, aspects of the present disclosure are not so limited. In other embodiments, a decision may be based on multiple pieces of information, such as facts extracted from report text, report metadata, data retrieved from patient health record, etc.

It should be appreciated that the guideline 500 shown in FIG. 5 and the decision tree 600 shown in FIG. 6 are provided solely for purposes of illustration, as other guidelines may also be used to create decision trees. Furthermore, a decision tree may be constructed in any suitable manner. For example, where a guideline calls for multiple independent decisions, such decisions may be made in any order. For instance, in the example of FIGS. 5-6, an alternative decision tree may be constructed by deciding at the root node whether the patient is high risk, and then deciding which of the four ranges the nodule size falls into.

The inventor has recognized and appreciated various disadvantages of conventional ways of presenting a guideline to a user. For example, the guideline 500 in the example of FIG. 5 is presented in a 2-dimensional table format. Where a guideline includes recommendations that depend on more than two items of information, multiple tables may be needed to present all of the possible combinations. For instance, if the recommendation in the example of FIG. 5 were to depend also on patient gender, two separate tables may be needed, one for male patients and another for female patients. If the number of variables (e.g., nodule size, patient risk category, patient gender, etc.) or the number of possible values for each variable is large, it may be time consuming for a user to identify the appropriate table.

Likewise, if the number of decisions to be made or the number of outcomes for each decision is large, a decision tree constructed in a similar manner as the decision tree 600 in the example of FIG. 6 may become large and unwieldy. A user may find such a tree confusing, and the process of manually resolving each decision node to identify a path through the tree may be time consuming and error prone.

Accordingly, the inventor has recognized and appreciated that it may be beneficial to provide a compact format to encapsulate the decision making process specified by a guideline. In some embodiments, a guideline format may include a component for specifying one or more items of information called for by a guideline (e.g., one or more facts relating to findings, symptoms, medical history, etc.). Additionally, or alternatively, a guideline format may include a component for specifying one or more recommendations (e.g., further diagnostic testing, follow up, symptom management, etc.), and/or a component for specifying how various situations (e.g., various combinations of findings, symptoms, medical history, etc.) are mapped to respective recommendations.

In some embodiments, a guideline format may include a decision rule format. As discussed above (e.g., in connection with FIGS. 2-3), a decision rule may be specified that maps a combination of one or more items of information to a corresponding recommendation called for by a guideline. Such a decision rule may be used to provide automatic assistance in verifying compliance with respect to the guideline. For example, a decision engine (e.g., the illustrative decision engine 270 in the example of FIG. 2) may be configured to apply one or more decision rules to one or more facts extracted from a report to determine whether the report includes an appropriate recommendation called for by the guideline.

In some embodiments, a decision rule format may be a markup language format such as an XML format. This may facilitate the development of decision rules separately from the development of a decision engine configured to receive decision rules as input.

FIG. 7 shows an illustrative decision rule 700 written in an XML format, in accordance with some embodiments. In this example, the decision rule 700 includes three components: the <features> component 705, the <end_points> component 710, and the <algorithm feature="root"> component 715.

In some embodiments, the <features> component 705 may declare one or more features (e.g., "uniformly_cystic," "size," "side," "size_changed," etc.), which may correspond to the items of information called for by a guideline (e.g., a radiology guideline relating to adrenal nodules). For example, a radiology guideline may specify that a radiologist indicate in a report whether the size of an adrenal nodule has changed. The radiologist may indicate that the size is unchanged, has increased, or has decreased, or there is no basis for determining whether the size has changed because the adrenal nodule has not been previously documented. This information may be captured by the feature "size_changed" (shown at 720), which may take on a number of different values such as "no_priors" and "increased."

In some embodiments, one or more synonyms may be provided for a value of a feature. For example, a radiologist may say, "the adrenal nodule is larger," or "the adrenal nodule has grown." Each of these expressions has the same meaning as, "the size of the adrenal nodule has increased." Accordingly, synonyms "larger" and "has grown" are provided (shown at 725) for the value "increased" of the feature "size_changed."

In some embodiments, the <end_points> component 710 may declare one or more end points (e.g., "cyst_no_recommendation"), which may correspond to the recommendations called for by a guideline. For example, if the end point denoted by "cyst_no_recommendation" (shown at 730) is reached, the correct recommendation called for by the guideline may be a surgery referral. In some embodiments, the correct recommendation may be provided, along with a template for an explanation of the basis of the recommendation, for example, as shown at 735. Any suitable explanation template may be used, including, but not limited to, a list of one or more items of information that led to the recommendation.

In some embodiments, the <algorithm feature="root"> component 715 may include one or more if statements and one or more else statements, which may correspond to decisions to be made under the guideline. For example, the if statement at 740 may be applied to determine if an adrenal nodule is present. If so, the following if statement may be applied to determine if the adrenal nodule is uniformly cystic. If so, the end point denoted by "cyst_no_recommendation" is reached at 745, and the recommendation specified at 735 is triggered.

In some embodiments, the <algorithm feature="root"> component 715 may include one or more if statements, but only else statement. The else statement may be associated with a default recommendation. Such a default recommendation may be triggered, for instance, when a report fails to provide all of the information called for by a guideline. In the example shown in FIG. 7, the feature "no_known_malignancy" (shown at 750) is used as a default and is reached when none of the preceding if statements leads no any end point with a recommendation. However, it should be appreciated that aspects of the present disclosure are not limited to the use of a default, nor to specifying a default using an else statement, as defaults may be specified in other manners.

While some details of implementation are described above in connection with the decision rule 700 of FIG. 7, it should be appreciated that such details are provided solely for purposes of illustration. For instance, aspects of the present disclosure are not limited to the use of decision rules written in an XML format, as other formats may also be suitable. Furthermore, aspects of the present disclosure are not limited to the use of synonyms. For example, in an embodiment in which an ontology is used by a CLU engine to process reports, the CLU engine may output a unique label for each concept in the ontology. For example, the CLU engine may output "no priors," even if the report states "no comparison" or "no history." In this manner, no synonym may be included in the decision rule.

Some guidelines may call for many pieces of information, and a medical professional may not always include in a report all of the information called for by a guideline. In some embodiments, a QA tool may automatically identify missing pieces of information (e.g., by applying one or more rules to report text and/or facts extracted from the report text by a CLU engine) and attempt to retrieve such information from one or more other sources (e.g., a repository of patient health records). However, some missing information may not be readily available, and the medical professional who prepared the report may be consulted in an attempt to obtain all of the missing information.

A medical professional may be prompted to provide additional information in any suitable manner, as aspects of the present disclosure are not limited in this respect. For example, in some embodiments, the medical professional may be explicitly prompted to provide multiple items of missing information one by one in a question-and-answer format. In some embodiments, a decision tree (e.g., the illustrative decision tree 600 in the example of FIG. 6) may be presented to the medical professional, and the medical professional may be prompted to "walk through" the tree and provide answers at one or more traversed nodes where information is missing.

However, the inventor has recognized and appreciated that it may be undesirable to interrupt a medical professional's workflow with frequent and/or prolonged interactions with a QA tool. For example, the above-described methods for prompting a medical professional to provide additional information may become inefficient and/or impractical if there is a large number of missing information items.

Accordingly, in some embodiments, assumed values may be automatically selected for the missing items of information and presented to the medical professional for confirmation. For example, the assumed values may be incorporated into a draft report and presented to the medical professional as part of a report review workflow. In this manner, the medical professional may simply confirm the assumed values or provide corrections thereto while he reviews the draft report, which may be less disruptive than providing the missing information through a separate process. However, it should be appreciated that aspects of the present disclosure are not limited to incorporating assumed values into a draft report, nor to presenting assumed values as part of a report review workflow, as other ways of presenting assumed values may also be suitable.

Figure 8:
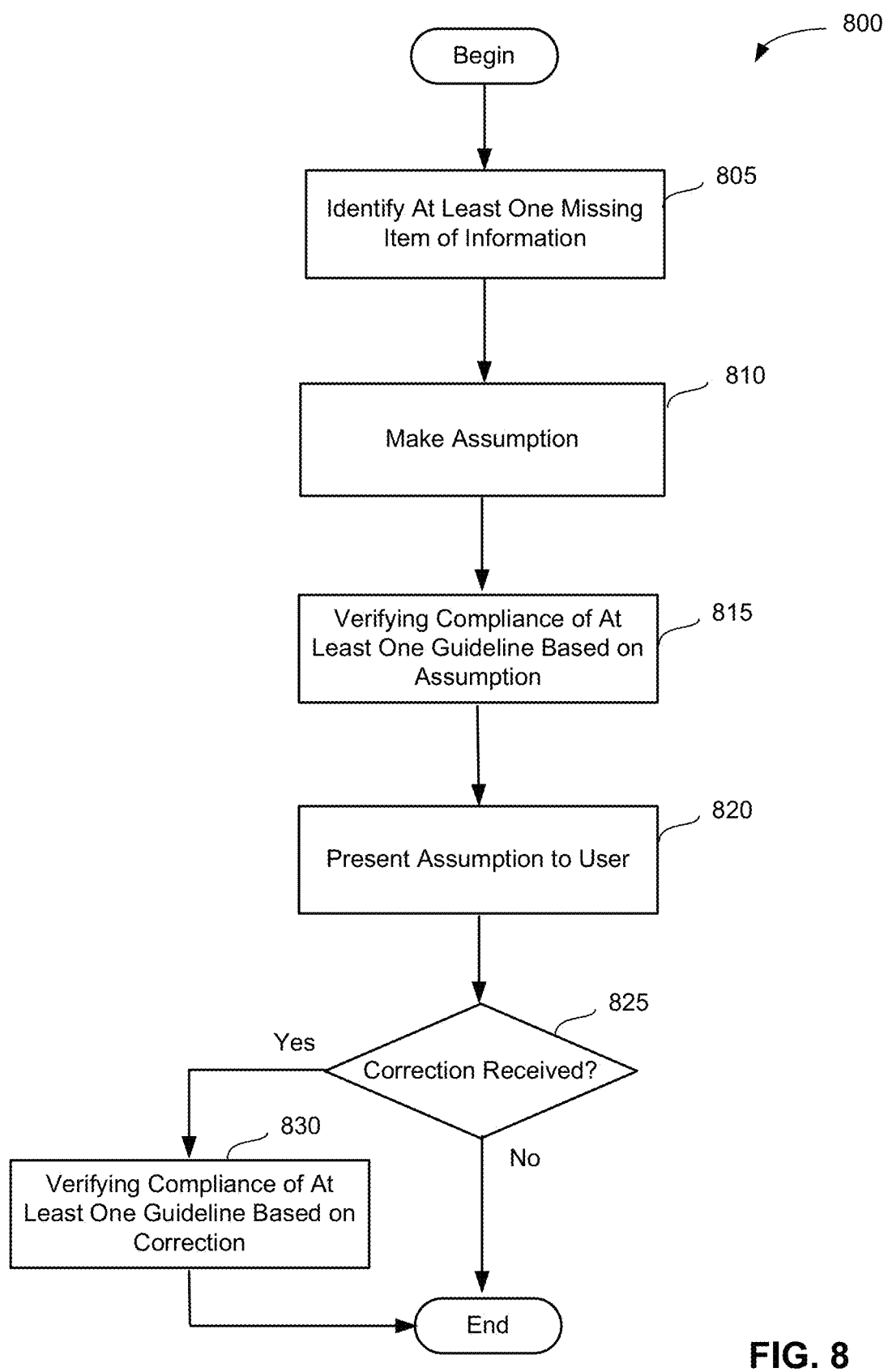
FIG. 8 shows an illustrative process 800 that may be performed to select and present assumed values, in accordance with some embodiments.

FIG. 8 shows an illustrative process 800 that may be performed to select and present assumed values, in accordance with some embodiments. For example, the process 800 may be performed by the illustrative QA tool 205 shown in FIG. 2 to facilitate verification of compliance with respect to one or more guidelines.

At act 805, a report provided by a medical professional may be analyzed to determine whether the report includes one or more desired items of information. For example, in some embodiments, one or more decision rules corresponding to a guideline may be applied to a narrative provided by the medical professional and/or one or more facts extracted from the narrative by a CLU engine to determine whether the report includes the information called for by the guideline. As a result, at least one missing item of information may be identified.

At act 810, an assumption may be made automatically with respect to the at least one missing item of information. This may be done in any suitable manner, as aspects of the present disclosure are not limited to any particular way of making assumptions for missing items of information. In some embodiments, an assumed value may be selected at least in part by looking up one or more records. For example, an assumption relating to a patient's demographic information or medical history may be made based on information retrieved from the patient's health record. In some embodiments, an assumption may be made based on what is known about the patient in conjunction with statistical observations from a relevant population. For example, if a radiologist preparing a report regarding a pulmonary nodule did not indicate whether the patient is a smoker or non-smoker, an assumption may be made that the patient is a non-smoker because it is known that the patient is a 65-year-old female and it is further known that a female aged between 50 and 60 is more likely to be a non-smoker than a smoker.

At act 815, a verification may be performed to determine whether the report complies with at least one guideline, and the assumption made at act 810 may be taken into account in the verification. For example, in some embodiments, one or more decision rules associated with the at least one guideline may be applied based on one or more assumed values to determine whether the report includes an appropriate recommendation called for by the at least one guideline.

At act 820, the assumption made at 810 is presented to a user for confirmation. The user may be the medical professional who provided the report being verified, or some other user (e.g., a supervisor). The assumption may be presented in any suitable manner, as aspects of the present disclosure are not limited in this respect. For instance, as discussed above, the assumption may be incorporated into a draft report (which may or may not be formatted according to one or more suitable guidelines) and may be presented as part of a report review process. Alternatively, the assumption may be presented outside the context of any draft report, for example, via a pop-up window or some other suitable user interface element.

At act 825, the user may be prompted to review the assumption presented at 820 and provide any necessary correction. If the user confirms the assumption, no further action may be taken. Alternatively, the assumption and/or any verification result based on the assumption obtained at act 815 may be accepted and further processing relating to the verification result may be performed (not shown).

If the user provides a correction at act 825, part or all of the verification performed at act 815 is automatically repeated at act 830, while the correction is taken into account. For example, in an embodiment in which one or more decision rules were applied at act 815, some or all of the decision rules may be reapplied dynamically based on the correction provided by the user. In some embodiments, repeating the verification may include generating a new draft report that incorporates the correction and/or any updated verification result. Any changes made in the draft report may be highlighted in a suitable manner (e.g., using strikeouts, underlining, etc.) to facilitate review by the user. However, it should be appreciated that aspects of the present disclosure are not limited to generating a new draft report, nor to highlighting changes in the draft report.

It should be appreciated that the illustrative process 800 shown in FIG. 8 and described above is merely one example of a process that may be performed to select and present assumed values. Aspects of the present disclosure are not limited to any detail described in connection with this example. For example, in various embodiments, a QA tool may make any suitable number of assumptions in connection with a report, or no assumption at all. Furthermore, in some embodiments, a QA tool may make an assumption and present it to a user for confirmation, without using the assumption to verify whether the report includes a recommendation called for by a guideline. For example, the assumption may be made solely for the purpose of ensuring that the report includes all of the information called for by a reporting guideline.

FIG. 9 shows an illustrative medical report 900 that may be analyzed using a QA tool to provide guidance to a medical professional (e.g., a radiologist), in accordance with some embodiments. For example, the illustrative medical report 900 may be analyzed by the illustrative QA tool 205 shown in FIG. 2 to facilitate compliance with respect to one or more guidelines.

In the example of FIG. 9, the illustrative medical report 900 discusses a CT scan performed on a patient's chest. At 905, the report states that the patient is a "65 female." In the "FINDINGS" section, the report recites "[a] 6 mm nodule is noted laterally in the left lower lobe" (at 910A), and "stable 2 mm nodule in the right middle lobe" (at 915A). Similarly, in the "IMPRESSION" section, the report describes an "indeterminate nodule in the left lower lobe" (at 910B) and "stable nodule in the right middle lobe" (at 915B). The "IMPRESSION" section also states, "follow up CT is recommended in 18 months" (at 920).

In some embodiments, the illustrative medical report 900 may be processed by a CLU engine to extract one or more facts. For example, the CLU engine may extract "65-year-old female" based on the portion of text at 905. As another example, the CLU engine may determine that the portions of text at 910A and 910B may be two mentions of the same entity (e.g., because both portions of text refer to "left lower lobe") and extract based on those portions of text "pulmonary nodule" and "6 mm." As another example, the CLU engine may extract "recommendation—follow up CT 18 months" based on the portion of text at 920.

In some embodiments, the CLU engine may be configured to extract only positive findings. For example, the CLU engine may determine that the portion of text at 915 does not represent a positive finding because it refers to a nodule that is characterized as "stable." As a result, the CLU engine may not include this nodule in the output of extracted facts. In alternative embodiments, the CLU may include such a finding in the output, along with some indication that the finding is determined not to be a positive finding.

In some embodiments, a decision engine (e.g., the illustrative decision engine 270 shown in FIG. 2) may be used to analyze the facts extracted by the CLU engine. As discussed above, a decision engine may in some embodiments be configured to make an assumption when an item of information called for by a guideline is not provided in a report. For example, the Fleischner guideline discussed above in connection with FIGS. 5-6 may call for different recommendations depending on whether the patient is low risk or high risk. Because the report 900 does not indicate whether the patient is low risk (e.g., non-smoker) or high risk (e.g., smoker), an assumption may be made that the patient is low risk, for example, because based on available statistics a 65-year-old female is more likely to be low risk (e.g., non-smoker).

In the example of FIG. 9, the decision engine may apply one or more decision rules corresponding to an appropriate guideline (e.g., the Fleischner guideline discussed above in connection with FIGS. 5-6) to the extracted facts, "pulmonary nodule" and "6 mm," and the assumption, "low risk," to determine one or more recommendations called for by the guideline (e.g., follow up CT in 12 months). It may then be determined that the recommendation in the report 900 (i.e., follow up CT in 18 months) is inconsistent with the guideline. An alert may be generated accordingly and presented to, for example, to the medical professional who prepared the report 900, or another medical professional (e.g., a supervisor, an ordering physician, etc.).

In some embodiments, the alert may be presented as part of a report review process. For example, a formatted report may be generated based on a narrative and/or discrete items of information provided by a medical professional, and/or one or more facts extracted from the narrative by a CLU engine. In some embodiments, the alert may be provided in the context of the formatted report, for example, by incorporating a recommendation called for by the guideline into the formatted report and highlighting or otherwise indicating that an inconsistent recommendation was made in the narrative provided by the medical professional. In alternative embodiments, the recommendation called for by the guideline may be displayed separately from the formatted report (e.g., in a separate window, panel, or other user interface element), but in a manner that links the recommendation called for by the guideline with the inconsistent recommendation appearing in the formatted report. Other ways of presenting an alert may also be suitable, as aspects of the present disclosure is not limited in this respect. For example, alerts may be presented audibly, instead of, or in addition to, being presented visually.

In some embodiments, an assumption made by a decision engine may be presented to a user for confirmation. In this manner, the user may be reminded of an item of information that he may have neglected to provide in the report 900. Additionally, in an embodiment in which an assumption is made based on statistical information, the decision engine may turn out to be correct in a large number of cases. The user may simply confirm the assumption in such cases, which may improve the efficiency of the report review workflow.

In some embodiments, a correction to an assumption provided by a user may cause the decision engine to automatically reapply some or all of the previously applied decision rules. For instance, in the example of FIG. 9, the user may indicates that the assumption of "low risk" is incorrect (e.g., because it is known that the patient is a smoker). As a result, the decision engine may automatically reapply at least one decision rule, such as a decision rule relating to the patient risk category. The decision engine may skip one or more other decision rules, such as a decision rule relating to nodule size because the correction does not affect the nodule size. Alternatively, the decision engine may reapply all decision rules.

In some embodiments, an updated recommendation may be provided to the user as a result of one or more decision rules being reapplied. For instance, in the example of FIG. 9, reapplying a decision rule corresponding to the Fleischner guideline based on the correction "high risk" results in an updated recommendation of follow up CT in 6-12 months, as opposed to the initial recommendation of follow up CT in 12 months. The updated recommendation may be presented to the user in any suitable manner, for example, by highlighting the changes using markings such as underlining for addition, strikeouts for deletion, etc. In some embodiments, the updated recommendation may also be presented in a manner that links the updated recommendation to the corresponding correction. For instance, in the example of FIG. 9, the updated recommendation of follow up CT in 6-12 months may be displayed using the same color as the correction "high risk" to indicates that the updated recommendation resulted from that correction.

Figure 10:
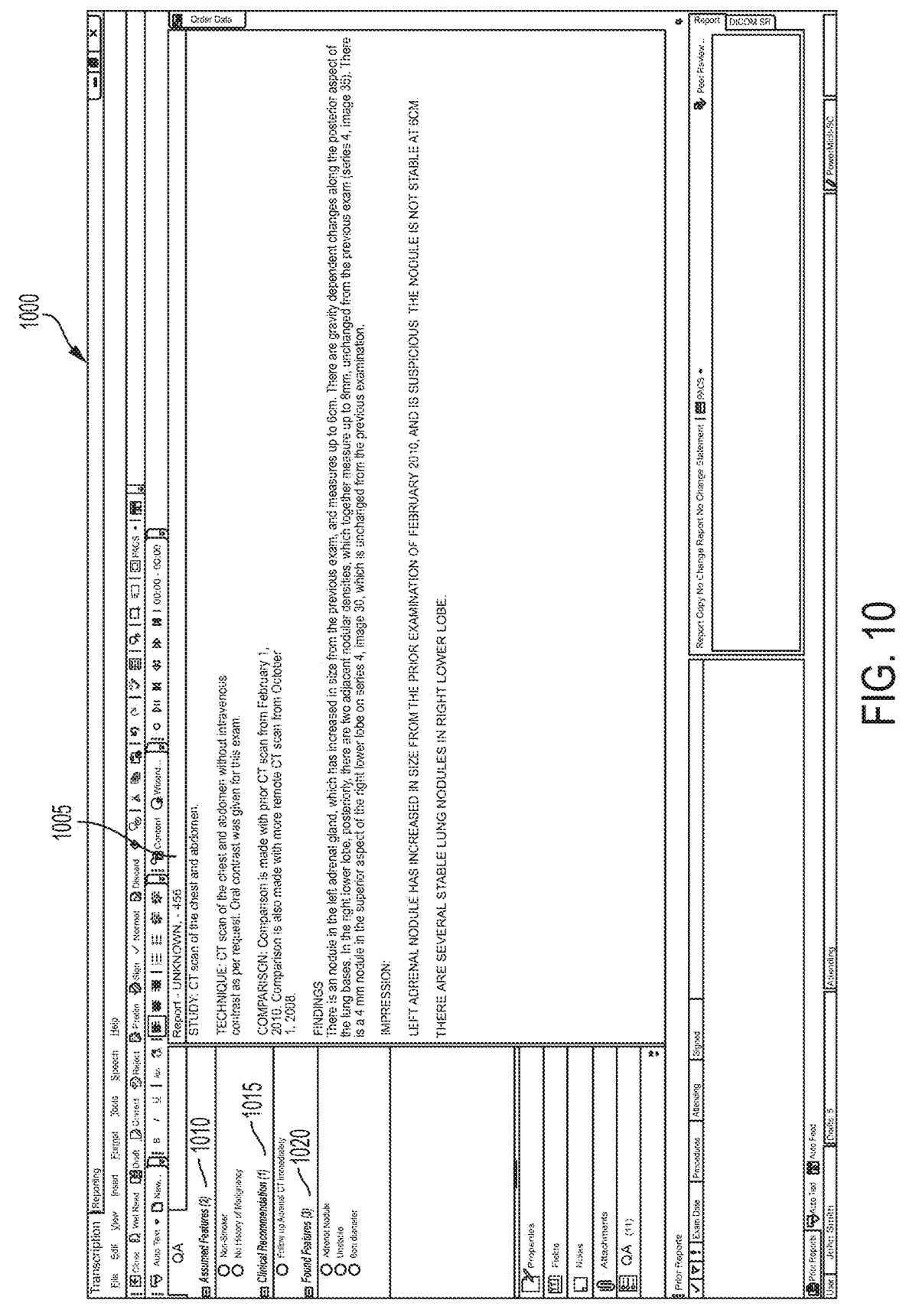

FIG. 10 shows an illustrative user interface 1000 for creating and/or reviewing medical reports, in accordance with some embodiments. In this example, the user interface 1000 includes a Report panel 1005 for displaying report text. In some embodiments, the displayed report text may be raw text typed by a medical professional (e.g., a radiologist), recognized from a handwritten note prepared by the medical professional, or transcribed from speech captured from the medical professional. In alternative embodiments, the displayed report text may be the result of processing and/or formatting raw text. For example, portions of raw text may be organized according to a template and/or modified to use desired terminology and/or wording.

In the example of FIG. 10, the user interface 1000 includes an Assumed Features panel 1010, a Clinical Recommendation panel 1015, and a Found Features panel 1020. The Assumed Features panel 1010 may be used to present one or more assumptions made by a decision engine, for example, in the process of verifying whether the report complies with one or more guidelines. The Found Features panel 1020 may be used to present one or more facts, for example, extracted from the report, provided by the medical professional through a point-and-click data entry interface, or otherwise obtained from a reliable source (e.g., a patient health record). In this manner, a user may be able to readily distinguish between assumptions and found facts, and may review the assumptions more closely to see whether any correction is needed.

In some embodiments, the Clinical Recommendation panel 1015 may be used to alert the user of any incomplete or incorrect recommendation. For instance, in the example of FIG. 10, the medical professional preparing the report may have neglected to provide any follow up recommendation. The decision engine may apply one or more decision rules to determine that, under an applicable guideline, a follow up adrenal CT should be performed immediately. This recommendation may be displayed in the Clinical Recommendation panel 1015, and may be included in a final report (not shown). Alternatively, or additionally, the user may be given an opportunity to either accept or reject the recommendation output by the decision engine.

Although some details of implementation are shown in FIGS. 9-10 and/or discussed above, it should be appreciated that aspects of the present disclosure are not limited to any particular manner of implementation. For example, a user interface for presenting medical reports may include any suitable combination of user interface elements (e.g., menus, panels, buttons, etc.) arranged in any suitable manner.

Below are detailed descriptions of illustrative medical fact extraction techniques that may be used in conjunction with various techniques described above for providing guidance to medical professionals, in accordance with some embodiments. For example, techniques for extracting medical facts may be used to facilitate the verification of a medical report for compliance with one or more guidelines, as discussed above in connection with FIG. 2.

Automatic extraction of medical facts from a free-form narration may be performed in any suitable way using any suitable technique(s), as aspects of the present disclosure are not limited in this respect. In some embodiments, pre-processing may be performed on a free-form narration prior to performing automatic fact extraction, for example, to determine the sequence of words represented by the free-form narration. Such pre-processing may also be performed in any suitable way using any suitable technique(s), as aspects of the present disclosure are not limited in this respect. For example, in some embodiments, the clinician may provide the free-form narration directly in textual form (e.g., using a keyboard or other text entry device), and the textual free-form narration may be automatically parsed to determine its sequence of words. In other embodiments, the clinician may provide the free-form narration in audio form as a spoken dictation, and an audio recording of the clinician's spoken dictation may be received and/or stored. The audio input may be processed in any suitable way prior to or in the process of performing fact extraction, as aspects of the present disclosure are not limited in this respect. In some embodiments, the audio input may be processed to form a textual representation, and fact extraction may be performed on the textual representation. Such processing to produce a textual representation may be performed in any suitable way. For example, in some embodiments, the audio recording may be transcribed by a human transcriptionist, while in other embodiments, automatic speech recognition (ASR) may be performed on the audio recording to obtain a textual representation of the free-form narration provided via the clinician's dictation. Any suitable automatic speech recognition technique may be used, as aspects of the present disclosure are not limited in this respect. In other embodiments, speech-to-text conversion of the clinician's audio dictation may not be required, as a technique that does not involve processing the audio to produce a textual representation may be used to determine what was spoken. In one example, the sequence of words that was spoken may be determined directly from the audio recording, e.g., by comparing the audio recording to stored waveform templates to determine the sequence of words. In other examples, the clinician's speech may not be recognized as words, but may be recognized in another form such as a sequence or collection of abstract concepts. It should be appreciated that the words and/or concepts represented in the clinician's free-form narration may be represented and/or stored as data in any suitable form, including forms other than a textual representation, as aspects of the present disclosure are not limited in this respect.

In some embodiments, one or more medical facts may be automatically extracted from the free-form narration (in audio or textual form) or from a pre-processed data representation of the free-form narration using a fact extraction component applying natural language understanding techniques. In some embodiments, the medical facts to be extracted may be defined by a set of fact categories (also referred to herein as "fact types" or "entity types") commonly used by clinicians in documenting patient encounters. In some embodiments, a suitable set of fact categories may be defined by any of various known healthcare standards. For example, in some embodiments, the medical facts to be extracted may include facts that are required to be documented by Meaningful Use standards promulgated by the U.S. government, e.g., under 42 C.F.R. § 495, which sets forth "Objectives" specifying items of medical information to be recorded for medical patients. Such facts currently required by the Meaningful Use standards include social history facts, allergy facts, diagnostic test result facts, medication facts, problem facts, procedure facts, and vital sign facts. However, these are merely illustrative, as aspects of the present disclosure are not limited to any particular set of fact categories. Some embodiments may not use one or more of the above-listed fact categories, and some embodiments may use any other suitable fact categories. Other non-limiting examples of suitable categories of medical facts include findings, disorders, body sites, medical devices, subdivided categories such as observable findings and measurable findings, etc. The fact extraction component may be implemented in any suitable form, as aspects of the present disclosure are not limited in this respect. Illustrative implementations for a fact extraction component are described in detail below.

One illustrative application for the techniques described herein is for use in a system for enhancing medical documentation processes. An illustrative operating environment for such a system is illustrated in FIG. 1. The illustrative operating environment includes a medical documentation system 100, which may be implemented in any suitable form, as aspects of the present disclosure are not limited in this respect. For example, system 100 may be implemented as a single stand-alone machine, or may be implemented by multiple distributed machines that share processing tasks in any suitable manner. System 100 may be implemented as one or more computers; an example of a suitable computer is described below. In some embodiments, system 100 may include one or more tangible, non-transitory computer-readable storage devices storing processor-executable instructions, and one or more processors that execute the processor-executable instructions to perform the functions described herein. The storage devices may be implemented as computer-readable storage media encoded with the processor-executable instructions; examples of suitable computer-readable storage media are discussed below.

As depicted, illustrative system 100 includes an ASR engine 102, a fact extraction component 104, and a fact review component 106. Each of these processing components of system 100 may be implemented in software, hardware, or a combination of software and hardware. Components implemented in software may comprise sets of processor-executable instructions that may be executed by the one or more processors of system 100 to perform the functionality described herein. Each of ASR engine 102, fact extraction component 104 and fact review component 106 may be implemented as a separate component of system 100, or any combination of these components may be integrated into a single component or a set of distributed components. In addition, any one of ASR engine 102, fact extraction component 104 and fact review component 106 may be implemented as a set of multiple software and/or hardware components. It should be understood that any such component depicted in FIG. 1 is not limited to any particular software and/or hardware implementation and/or configuration.

As illustrated in FIG. 1, user interface 110 is presented to a clinician 120, who may be a physician, a physician's aide, a nurse, or any other personnel involved in the evaluation and/or treatment of a patient 122 in a clinical setting. During the course of a clinical encounter with patient 122, or at some point thereafter, clinician 120 may wish to document the patient encounter. Such a patient encounter may include any interaction between clinician 120 and patient 122 in a clinical evaluation and/or treatment setting, including, but not limited to, an office visit, an interaction during hospital rounds, an outpatient or inpatient procedure (surgical or non-surgical), a follow-up evaluation, a visit for laboratory or radiology testing, etc. One method that clinician 120 may use to document the patient encounter may be to enter medical facts that can be ascertained from the patient encounter into user interface 110 as discrete structured data items. The set of medical facts, once entered, may be transmitted in some embodiments via any suitable communication medium or media (e.g., local and/or network connection(s) that may include wired and/or wireless connection(s)) to system 100. Specifically, in some embodiments, the set of medical facts may be received at system 100 by a fact review component 106, illustrative functions of which are described below.

Another method that may be used by clinician 120 to document the patient encounter is to provide a free-form narration of the patient encounter. In some embodiments, the narration may be free-form in the sense that clinician 120 may be unconstrained with regard to the structure and content of the narration, and may be free to provide any sequence of words, sentences, paragraphs, sections, etc., that he would like. In some embodiments, there may be no limitation on the length of the free-form narration, or the length may be limited only by the processing capabilities of the user interface into which it is entered or of the later processing components that will operate upon it. In other embodiments, the free-form narration may be constrained in length (e.g., limited to a particular number of characters).

A free-form narration of the patient encounter may be provided by clinician 120 in any of various ways. One way may be to manually enter the free-form narration in textual form into user interface 110, e.g., using a keyboard. In this respect, the one or more processors of system 100 and/or of a client device in communication with system 100 may in some embodiments be programmed to present a user interface including a text editor/word processor to clinician 120. Such a text editor/word processor may be implemented in any suitable way, as aspects of the present disclosure are not limited in this respect.

Another way to provide a free-form narration of the patient encounter may be to verbally speak a dictation of the patient encounter. Such a spoken dictation may be provided in any suitable way, as aspects of the present disclosure are not limited in this respect. As illustrated in FIG. 1, one way that clinician 120 may provide a spoken dictation of the free-form narration may be to speak the dictation into a microphone 112 providing input (e.g., via a direct wired connection, a direct wireless connection, or via a connection through an intermediate device) to user interface 110. An audio recording of the spoken dictation may then be stored in any suitable data format, and transmitted to system 100 and/or to medical transcriptionist 130. Another way that clinician 120 may provide the spoken dictation may be to speak into a telephone 118, from which an audio signal may be transmitted to be recorded at system 100, at the site of medical transcriptionist 130, or at any other suitable location. Alternatively, the audio signal may be recorded in any suitable data format at an intermediate facility, and the audio data may then be relayed to system 100 and/or to medical transcriptionist 130.

In some embodiments, medical transcriptionist 130 may receive the audio recording of the dictation provided by clinician 120, and may transcribe it into a textual representation of the free-form narration (e.g., into a text narrative). Medical transcriptionist 130 may be any human who listens to the audio dictation and writes or types what was spoken into a text document. In some embodiments, medical transcriptionist 130 may be specifically trained in the field of medical transcription, and may be well-versed in medical terminology. In some embodiments, medical transcriptionist 130 may transcribe exactly what she hears in the audio dictation, while in other embodiments, medical transcriptionist 130 may add formatting to the text transcription to comply with generally accepted medical document standards. When medical transcriptionist 130 has completed the transcription of the free-form narration into a textual representation, the resulting text narrative may in some embodiments be transmitted to system 100 or any other suitable location (e.g., to a storage location accessible to system 100). Specifically, in some embodiments the text narrative may be received from medical transcriptionist 130 by fact extraction component 104 within system 100. Illustrative functionality of fact extraction component 104 is described below.

In some other embodiments, the audio recording of the spoken dictation may be received, at system 100 or any other suitable location, by automatic speech recognition (ASR) engine 102. In some embodiments, ASR engine 102 may then process the audio recording to determine what was spoken. As discussed above, such processing may involve any suitable speech recognition technique, as aspects of the present disclosure are not limited in this respect. In some embodiments, the audio recording may be automatically converted to a textual representation, while in other embodiments, words identified directly from the audio recording may be represented in a data format other than text, or abstract concepts may be identified instead of words. Examples of further processing are described below with reference to a text narrative that is a textual representation of the free-form narration; however, it should be appreciated that similar processing may be performed on other representations of the free-form narration as discussed above. When a textual representation is produced, in some embodiments it may be reviewed by a human (e.g., a transcriptionist) for accuracy, while in other embodiments the output of ASR engine 102 may be accepted as accurate without human review. As discussed above, some embodiments are not limited to any particular method for transcribing audio data; an audio recording of a spoken dictation may be transcribed manually by a human transcriptionist, automatically by ASR, or semi-automatically by human editing of a draft transcription produced by ASR. Transcriptions produced by ASR engine 102 and/or by transcriptionist 130 may be encoded or otherwise represented as data in any suitable form, as aspects of the present disclosure are not limited in this respect.

In some embodiments, ASR engine 102 may make use of a lexicon of medical terms (which may be part of, or in addition to, another more general speech recognition lexicon) while determining the sequence of words that were spoken in the free-form narration provided by clinician 120. However, aspects of the present disclosure are not limited to the use of a lexicon, or any particular type of lexicon, for ASR. When used, the medical lexicon in some embodiments may be linked to a knowledge representation model such as a clinical language understanding ontology utilized by fact extraction component 104, such that ASR engine 102 might produce a text narrative containing terms in a form understandable to fact extraction component 104. In some embodiments, a more general speech recognition lexicon might also be shared between ASR engine 102 and fact extraction component 104. However, in other embodiments, ASR engine 102 may not have any lexicon developed to be in common with fact extraction component 104. In some embodiments, a lexicon used by ASR engine 102 may be linked to a different type of medical knowledge representation model, such as one not designed or used for language understanding. It should be appreciated that any lexicon used by ASR engine 102 and/or fact extraction component 104 may be implemented and/or represented as data in any suitable way, as aspects of the present disclosure are not limited in this respect.

In some embodiments, a text narrative, whether produced by ASR engine 102 (and optionally verified or not by a human), produced by medical transcriptionist 130, directly entered in textual form through user interface 110, or produced in any other way, may be re-formatted in one or more ways before being received by fact extraction component 104. Such re-formatting may be performed by ASR engine 102, by a component of fact extraction component 104, by a combination of ASR engine 102 and fact extraction component 104, or by any other suitable software and/or hardware component. In some embodiments, the re-formatting may be performed in a way known to facilitate fact extraction, and may be performed for the purpose of facilitating the extraction of clinical facts from the text narrative by fact extraction component 104. For example, in some embodiments, processing to perform fact extraction may be improved if sentence boundaries in the text narrative are accurate. Accordingly, in some embodiments, the text narrative may be re-formatted prior to fact extraction to add, remove or correct one or more sentence boundaries within the text narrative. In some embodiments, this may involve altering the punctuation in at least one location within the text narrative. In another example, fact extraction may be improved if the text narrative is organized into sections with headings, and thus the re-formatting may include determining one or more section boundaries in the text narrative and adding, removing or correcting one or more corresponding section headings. In some embodiments, the re-formatting may include normalizing one or more section headings (which may have been present in the original text narrative and/or added or corrected as part of the re-formatting) according to a standard for the healthcare institution corresponding to the patient encounter (which may be an institution-specific standard or a more general standard for section headings in clinical documents). In some embodiments, a user (such as clinician 120, medical transcriptionist 130, or another user) may be prompted to approve the re-formatted text.

Any suitable technique(s) for implementing re-formatting, examples of which are described above, may be employed, as aspects of the present disclosure are not limited in this respect. One illustrative technique suitable for performing re-formatting of a text narrative is described in U.S. patent application Ser. No. 11/322,971, filed on Dec. 30, 2005, entitled "Translating Literal Speech to Formatted Text", which is incorporated herein by reference in its entirety. Another illustrative technique that may be used in some embodiments for performing re-formatting of a text narrative involves the use of word N-gram statistical models to predict sentence and/or section boundaries in a text narrative. Such statistical models may be trained on a corpus of documents (e.g., past medical records) with correct punctuation and/or section headings (e.g., supplied by a medical transcriptionist).

In some embodiments, a statistical model may add punctuation (e.g., periods, exclamation points, question marks, etc.) to add one or more sentence boundaries to a text narrative by computing a probability, for each word in the text narrative, that a particular punctuation mark should follow that word. In computing the probability that a word should be followed by a punctuation mark, the statistical model may consider the N-word sequence from the text narrative that ends with that word, and determine the frequency with which that N-word sequence is followed by that punctuation mark in the training data for the statistical model. A lattice may then be constructed using the computed probabilities for all the words in the text narrative, or in a portion of the text narrative, and the best path in terms of combined probability through the lattice may be determined. Where punctuation marks are located in the best path through the lattice, those punctuation marks may be added in those locations to the text narrative in producing the formatted text. In some embodiments, another statistical model may add section headings, corresponding to section boundaries, in a similar fashion. For example, in some embodiments, a statistical model for section headings may compute probabilities, for each word, that the word should be followed by a section boundary. In some embodiments, in computing probabilities, a statistical model for section headings may consider more words that follow the current word than words that precede the current word. In some embodiments, one or more separate statistical models may be trained to delete incorrect sentence and/or section boundaries. Those models in some embodiments may be trained through feedback from clinician 120 or another user, by observing word sequences (initially including punctuation and/or section boundaries) from which clinician 120 or another user tends to remove the punctuation and/or section boundaries when editing.

In some embodiments, either an original or a re-formatted text narrative may be received by fact extraction component 104, which may perform processing to extract one or more medical facts from the text narrative. The text narrative may be received from ASR engine 102, from medical transcriptionist 130, directly from clinician 120 via user interface 110, or in any other suitable way. Any suitable technique(s) for extracting facts from the text narrative may be used, as aspects of the present disclosure are not limited in this respect. Illustrative techniques for medical fact extraction are described below.

In some embodiments, a fact extraction component may make use of one or more ontologies linked to one or more lexicons of medical terms. An ontology may be implemented as a relational database, or in any other suitable form, and may represent semantic concepts relevant to the medical domain. In some embodiments, such an ontology may also represent linguistic concepts related to ways the semantic concepts may be expressed in natural language.

In some embodiments, concepts in an ontology used by a fact extraction component may be linked to a lexicon of medical terms and/or codes, such that each medical term and each code is linked to at least one concept in the formal ontology. In some embodiments, the lexicon may include the standard medical terms and/or codes used by the institution in which the fact extraction component is applied. For example, the standard medical terms and/or codes used by an EHR maintained by the institution may be included in the lexicon linked to an ontology. In some embodiments, the lexicon may also include additional medical terms used by the various clinicians within the institution, and/or used by clinicians generally, when describing medical issues in a free-form narration. Such additional medical terms may be linked, along with their corresponding standard medical terms, to the appropriate shared concepts within the ontology. For example, the standard term "acute myocardial infarction" as well as other corresponding terms such as "heart attack", "acute MI" and "AMI" may all be linked to the same concept in the ontology—a concept representing an interruption of blood supply to the heart. Such linkage of multiple medical terms to the same concept in some embodiments may relieve the clinician of the burden of ensuring that only standard medical terms preferred by the institution appear in the free-form narration. For example, in some embodiments, a clinician may be free to use the abbreviation "AMI" or the colloquial "heart attack" in his free-form narration, and the shared concept linkage may allow the fact extraction component to nevertheless automatically extract a fact corresponding to "acute myocardial infarction".

In some embodiments, an ontology used by a fact extraction component may also represent various types of relationships between the concepts represented. One type of relationship between two concepts may be a parent-child relationship (also called a hypernym-hyponym relationship), in which the child concept is a more specific version of the parent concept. More formally, in a parent-child relationship, the child concept inherits all necessary properties of the parent concept, while the child concept may have necessary properties that are not shared by the parent concept. For example, "heart failure" may be a parent concept, and "congestive heart failure" may be a child concept of "heart failure." Parent-child relationships, or equivalently hypernym-hyponym relationships, are also often referred to as "is-a" relationships, reflecting the fact that the hyponym (the child) is a type of the hypernym (the parent) (e.g., "congestive heart failure" is a type of "heart failure"). In some embodiments, any other type(s) of relationship useful to the process of medical documentation may also be represented in an ontology. For example, one type of relationship may be a symptom relationship. In one example of a symptom relationship, a concept linked to the term "chest pain" may have a relationship of "is-symptom-of" to the concept linked to the term "heart attack". Other types of relationships may include complication relationships, comorbidity relationships, interaction relationships (e.g., among medications), and many others. Any number and type(s) of concept relationships may be included in such an ontology, as aspects of the present disclosure are not limited in this respect.

Alternatively or additionally, in some embodiments a fact extraction component may make use of one or more statistical models to extract semantic entities from natural language input. In general, a statistical model can be described as a functional component designed and/or trained to analyze new inputs based on probabilistic patterns observed in prior training inputs. In this sense, statistical models differ from "rule-based" models, which typically apply hard-coded deterministic rules to map from inputs having particular characteristics to particular outputs. By contrast, a statistical model may operate to determine a particular output for an input with particular characteristics by considering how often (e.g., with what probability) training inputs with those same characteristics (or similar characteristics) were associated with that particular output in the statistical model's training data. To supply the probabilistic data that allows a statistical model to extrapolate from the tendency of particular input characteristics to be associated with particular outputs in past examples, statistical models are typically trained (or "built") on large training corpuses with great numbers of example inputs. Typically the example inputs are labeled with the known outputs with which they should be associated, usually by a human labeler with expert knowledge of the domain. Characteristics of interest (known as "features") are identified ("extracted") from the inputs, and the statistical model learns the probabilities with which different features are associated with different outputs, based on how often training inputs with those features are associated with those outputs. When the same features are extracted from a new input (e.g., an input that has not been labeled with a known output by a human), the statistical model can then use the learned probabilities for the extracted features (as learned from the training data) to determine which output is most likely correct for the new input. Illustrative implementations of a fact extraction component using one or more statistical models are described further below.

In some embodiments, fact extraction component 104 may utilize a statistical fact extraction model based on entity detection and/or tracking techniques, such as those disclosed in: Florian, R., Hassan, H., Ittycheriah, A., Jing, H., Kambhatla, N., Luo, X., Nicolov, N., and Roukos, S. (2004). *A Statistical Model for Multilingual Entity Detection and Tracking.* Proceedings of the Human Language Technologies Conference 2004 (HLT-NAACL'04). This publication is incorporated herein by reference in its entirety.

For example, in some embodiments, a list of fact types of interest for generating medical reports may be defined, e.g., by a developer of fact extraction component 104. Such fact types (also referred to herein as "entity types") may include, for example, problems, disorders (a disorder is a type of problem), diagnoses (a diagnosis may be a disorder that a clinician has identified as a problem for a particular patient), findings (a finding is a type of problem that need not be a disorder), medications, body sites, social history facts, allergies, diagnostic test results, vital signs, procedures, procedure steps, observations, devices, and/or any other suitable medical fact types. It should be appreciated that any suitable list of fact types may be utilized, and may or may not include any of the fact types listed above, as aspects of the present disclosure are not limited in this respect. In some embodiments, spans of text in a set of sample patient encounter reports may be labeled (e.g., by a human) with appropriate fact types from the list. A statistical model may then be trained on the corpus of labeled sample reports to detect and/or track such fact types as semantic entities, using entity detection and/or tracking techniques, examples of which are described below.

For example, in some embodiments, a large number of past free-form narrations created by clinicians may be manually labeled to form a corpus of training data for a statistical entity detection model. As discussed above, in some embodiments, a list of suitable entities may be defined (e.g., by a domain administrator) to include medical fact types that are to be extracted from future clinician narrations. One or more human labelers (e.g., who may have specific knowledge about medical information and typical clinician narration content) may then manually label portions of the training texts with the particular defined entities to which they correspond. For example, given the training text, "Patient is complaining of acute sinusitis," a human labeler may label the text portion "acute sinusitis" with the entity label "Problem." In another example, given the training text, "He has sinusitis, which appears to be chronic," a human labeler may label the text "sinusitis" and "chronic" with a single label indicating that both words together correspond to a "Problem" entity. As should be clear from these examples, the portion of the text labeled as corresponding to a single conceptual entity need not be formed of contiguous words, but may have words split up within the text, having non-entity words in between.

In some embodiments, the labeled corpus of training data may then be processed to build a statistical model trained to detect mentions of the entities labeled in the training data. Each time the same conceptual entity appears in a text, that appearance is referred to as a mention of that entity. For example, consider the text, "Patient has sinusitis. His sinusitis appears to be chronic." In this example, the entity detection model may be trained to identify each appearance of the word "sinusitis" in the text as a separate mention of the same "Problem" entity.

In some embodiments, the process of training a statistical entity detection model on labeled training data may involve a number of steps to analyze each training text and probabilistically associate its characteristics with the corresponding entity labels. In some embodiments, each training text (e.g., free-form clinician narration) may be tokenized to break it down into various levels of syntactic substructure. For example, in some embodiments, a tokenizer module may be implemented to designate spans of the text as representing structural/syntactic units such as document sections, paragraphs, sentences, clauses, phrases, individual tokens, words, sub-word units such as affixes, etc. In some embodiments, individual tokens may often be single words, but some tokens may include a sequence of more than one word that is defined, e.g., in a dictionary, as a token. For example, the term "myocardial infarction" could be defined as a token, although it is a sequence of more than one word. In some embodiments, a token's identity (i.e., the word or sequence of words itself) may be used as a feature of that token. In some embodiments, the token's placement within particular syntactic units in the text (e.g., its section, paragraph, sentence, etc.) may also be used as features of the token.

In some embodiments, an individual token within the training text may be analyzed (e.g., in the context of the surrounding sentence) to determine its part of speech (e.g., noun, verb, adjective, adverb, preposition, etc.), and the token's part of speech may be used as a further feature of that token. In some embodiments, each token may be tagged with its part of speech, while in other embodiments, not every token may be tagged with a part of speech. In some embodiments, a list of relevant parts of speech may be pre-defined, e.g., by a developer of the statistical model, and any token having a part of speech listed as relevant may be tagged with that part of speech. In some embodiments, a parser module may be implemented to determine the syntactic structure of sentences in the text, and to designate positions within the sentence structure as features of individual tokens. For example, in some embodiments, the fact that a token is part of a noun phrase or a verb phrase may be used as a feature of that token. Any type of parser may be used, non-limiting examples of which include a bottom-up parser and/or a dependency parser, as aspects of the present disclosure are not limited in this respect.

In some embodiments, section membership may be used as a feature of a token. In some embodiments, a section normalization module may be implemented to associate various portions of the narrative text with the proper section to which it should belong. In some embodiments, a set of standardized section types (e.g., identified by their section headings) may be defined for all texts, or a different set of normalized section headings may be defined for each of a number of different types of texts (e.g., corresponding to different types of documents). For example, in some embodiments, a different set of normalized section headings may be defined for each type of medical document in a defined set of medical document types. Non-limiting examples of medical document types include consultation reports, history & physical reports, discharge summaries, and emergency room reports, although there are also many other examples. In the medical field, the various types of medical documents are often referred to as "work types." In some cases, the standard set of sections for various types of medical documents may be established by a suitable system standard, institutional standard, or more widely applicable standard, such as the Meaningful Use standard (discussed above) or the Logical Observation Identifiers Names and Codes (LOINC) standard maintained by the Regenstrief Institute. For example, an expected set of section headings for a history & physical report under the Meaningful Use standard may include headings for a "Reason for Visit" section, a "History of Present Illness" section, a "History of Medication Use" section, an "Allergies, Adverse Reactions and Alerts" section, a "Review of Systems" section, a "Social History" section, a "Physical Findings" section, an "Assessment and Plan" section, and/or any other suitable section(s). Any suitable set of sections may be used, however, as aspects of the present disclosure are not limited in this respect.

A section normalization module may use any suitable technique to associate portions of text with normalized document sections, as aspects of the present disclosure are not limited in this respect. In some embodiments, the section normalization module may use a table (e.g., stored as data in a storage medium) to map text phrases that commonly occur in medical documents to the sections to which they should belong. In another example, a statistical model may be trained to determine the most likely section for a portion of text based on its semantic content, the semantic content of surrounding text portions, and/or the expected semantic content of the set of normalized sections. In some embodiments, once a normalized section for a portion of text has been identified, the membership in that section may be used as a feature of one or more tokens in that portion of text.

In some embodiments, other types of features may be extracted, i.e., identified and associated with tokens in the training text. For example, in some embodiments, an N-gram feature may identify the previous (N–1) words and/or tokens in the text as a feature of the current token. In another example, affixes (e.g., suffixes such as -ectomy, -oma, -itis, etc.) may be used as features of tokens. In another example, one or more predefined dictionaries and/or ontologies may be accessed, and a token's membership in any of those dictionaries may be used as a feature of that token. For example, a predefined dictionary of surgical procedures may be accessed, and/or a dictionary of body sites, and/or a dictionary of known diseases, etc. In some embodiments, related concepts in an ontology may be used as features of a token, as described further below. It should be appreciated, however, that all of the foregoing feature types are merely examples, and any suitable number and/or types of features of interest may be designated, e.g., by a developer of the statistical entity detection model, as aspects of the present disclosure are not limited in this respect.

In some embodiments, the corpus of training text with its hand-labeled fact type entity labels, along with the collection of features extracted for tokens in the text, may be input to the statistical entity detection model for training. As discussed above, examples of suitable features include position within document structure, syntactic structure, parts of speech, parser features, N-gram features, affixes (e.g., prefixes and/or suffixes), membership in dictionaries (sometimes referred to as "gazetteers") and/or ontologies, surrounding token contexts (e.g., a certain number of tokens to the left and/or right of the current token), orthographic features (e.g., capitalization, letters vs. numbers, etc.), entity labels assigned to previous tokens in the text, etc. As one non-limiting example, consider the training sentence, "Patient is complaining of acute sinusitis," for which the word sequence "acute sinusitis" was hand-labeled as being a "Problem" entity. In one illustrative implementation, features extracted for the token "sinusitis" may include the token identity feature that the word is "sinusitis," a syntactic feature specifying that the token occurred at the end of a sentence (e.g., followed by a period), a part-of-speech feature of "noun," a parser feature that the token is part of a noun phrase ("acute sinusitis"), a trigram feature that the two preceding words are "of acute," an affix feature of "-itis," and a dictionary feature that the token is a member of a predefined dictionary of types of inflammation. It should be appreciated, however, that the foregoing list of features is merely illustrative, as any suitable features may be used. Aspects of the present disclosure are not limited to any of the features listed above, and implementations including some, all, or none of the above features, as well as implementations including features not listed above, are possible.

In some embodiments, given the extracted features and manual entity labels for the entire training corpus as input, the statistical entity detection model may be trained to be able to probabilistically label new texts (e.g., texts not included in the training corpus) with automatic entity labels using the same feature extraction technique that was applied to the training corpus. In other words, by processing the input features and manual entity labels of the training corpus, the statistical model may learn probabilistic relationships between the features and the entity labels. When later presented with an input text without manual entity labels, the statistical model may then apply the same feature extraction techniques to extract features from the input text, and may apply the learned probabilistic relationships to automatically determine the most likely entity labels for word sequences in the input text. Any suitable statistical modeling technique may be used to learn such probabilistic relationships, as aspects of the present disclosure are not limited in this respect. Non-limiting examples of suitable known statistical modeling techniques include machine learning techniques such as maximum entropy modeling, support vector machines, and conditional random fields, among others.

In some embodiments, training the statistical entity detection model may involve learning, for each extracted feature, a probability with which tokens having that feature are associated with each entity type. For example, for the suffix feature "-itis," the trained statistical entity detection model may store a probability p1 that a token with that feature should be labeled as being part of a "Problem" entity, a probability p2 that a token with that feature should be labeled as being part of a "Medication" entity, etc. In some embodiments, such probabilities may be learned by determining the frequency with which tokens having the "-itis" feature were hand-labeled with each different entity label in the training corpus. In some embodiments, the probabilities may be normalized such that, for each feature, the probabilities of being associated with each possible entity (fact type) may sum to 1. However, aspects of the present disclosure are not limited to such normalization. In some embodiments, each feature may also have a probability p0 of not being associated with any fact type, such that the non-entity probability p0 plus the probabilities of being associated with each possible fact type sum to 1 for a given feature. In other embodiments, separate classifiers may be trained for each fact type, and the classifiers may be run in parallel. For example, the "-itis" feature may have probability p1 of being part of a "Problem" entity and probability (1−p1) of not being part of a "Problem" entity, probability p2 of being part of a "Medication" entity and probability (1−p2) of not being part of a "Medication" entity, and so on. In some embodiments, training separate classifiers may allow some word sequences to have a non-zero probability of being labeled with more than one fact type simultaneously; for example, "kidney failure" could be labeled as representing both a Body Site and a Problem. In some embodiments, classifiers may be trained to identify sub-portions of an entity label. For example, the feature "-itis" could have a probability $p_B$ of its token being at the beginning of a "Problem" entity label, a probability $p_I$ of its token being inside a "Problem" entity label (but not at the beginning of the label), and a probability $p_O$ of its token being outside a "Problem" entity label (i.e., of its token not being part of a "Problem" entity).

In some embodiments, the statistical entity detection model may be further trained to weight the individual features of a token to determine an overall probability that it should be associated with a particular entity label. For example, if the token "sinusitis" has n extracted features f1 ... fn having respective probabilities p1 ... pn of being associated with a "Problem" entity label, the statistical model may be trained to apply respective weights w1 ... wn to the feature probabilities, and then combine the weighted feature probabilities in any suitable way to determine the overall probability that "sinusitis" should be part of a "Problem" entity. Any suitable technique for determining such weights may be used, including known modeling techniques such as maximum entropy modeling, support vector machines, conditional random fields, and/or others, as aspects of the present disclosure are not limited in this respect.

In some embodiments, when an unlabeled text is input to the trained statistical entity detection model, the model may process the text to extract features and determine probabilities for individual tokens of being associated with various entity (e.g., fact type) labels. In some embodiments, the most probable label (including the non-entity label, if it is most probable) may be selected for each token in the input text. In other embodiments, labels may be selected through more contextual analysis, such as at the phrase level or sentence level, rather than at the token level. Any suitable technique, such as Viterbi techniques, or any other suitable technique, may be used, as aspects of the present disclosure are not limited in this respect. In some embodiments, a lattice may be constructed of the associated probabilities for all entity types for all tokens in a sentence, and the best (e.g., highest combined probability) path through the lattice may be selected to determine which word sequences in the sentence are to be automatically labeled with which entity (e.g., fact type) labels. In some embodiments, not only the best path may be identified, but also the (N−1)-best alternative paths with the next highest associated probabilities. In some embodiments, this may result in an N-best list of alternative hypotheses for fact type labels to be associated with the same input text.

In some embodiments, a statistical model may also be trained to associate fact types extracted from new reports with particular facts to be extracted from those reports (e.g., to determine a particular concept represented by the text portion that has been labeled as an entity mention). For example, in some embodiments, a statistical fact extraction model may be applied to automatically label "acute sinusitis" not only with the "Problem" entity (fact type) label, but also with a label indicating the particular medical fact (e.g., concept) indicated by the word sequence (e.g., the medical fact "sinusitis, acute"). In such embodiments, for example, a single statistical model may be trained to detect specific particular facts as individual entities. For example, in some embodiments, the corpus of training text may be manually labeled by one or more human annotators with labels indicating specific medical facts, rather than labels indicating more general entities such as fact types or categories. However, in other embodiments, the process of detecting fact types as entities may be separated from the process of relating detected fact types to particular facts. For example, in some embodiments, a separate statistical model (e.g., an entity detection model) may be trained to automatically label portions of text with fact type labels, and another separate statistical model (e.g., a relation model) may be trained to identify which labeled entity (fact type) mentions together indicate a single specific medical fact. In some cases, the relation model may identify particular medical facts by relating together two or more mentions labeled with the same entity type.

For example, in the text, "Patient is complaining of acute sinusitis," in some embodiments an entity detection model may label the tokens "acute" and "sinusitis" as being part of a "Problem" entity. In some embodiments, a relation model, given that "acute" and "sinusitis" have been labeled as "Problem," may then relate the two tokens together to a single medical fact of "sinusitis, acute." For another example, consider the text, "Patient has sinusitis, which appears to be chronic." In some embodiments, an entity detection model may be applied to label the tokens "sinusitis" and "chronic" as "Problem" entity mentions.

In some embodiments, a relation model may then be applied to determine that the two "Problem" entity mentions "sinusitis" and "chronic" are related (even though they are not contiguous in the text) to represent a single medical fact of "sinusitis, chronic." For yet another example, consider the text, "She has acute sinusitis; chronic attacks of asthma may be a factor." In some embodiments, an entity detection model may label each of the tokens "acute," "sinusitis," "chronic," and "asthma" as belonging to "Problem" entity mentions. In some embodiments, a relation model may then be applied to determine which mentions relate to the same medical fact. For example, the relation model may determine that the tokens "acute" and "sinusitis" relate to a first medical fact (e.g., "sinusitis, acute"), while the tokens "chronic" and "asthma" relate to a different medical fact (e.g., "asthma, chronic"), even though the token "chronic" is closer in the sentence to the token "sinusitis" than to the token "asthma."

In some embodiments, a relation model may be trained statistically using methods similar to those described above for training the statistical entity detection model. For example, in some embodiments, training texts may be manually labeled with various types of relations between entity mentions and/or tokens within entity mentions. For example, in the training text, "Patient has sinusitis, which appears to be chronic," a human annotator may label the "Problem" mention "chronic" as having a relation to the "Problem" mention "sinusitis," since both mentions refer to the same medical fact. In some embodiments, the relation annotations may simply indicate that certain mentions are related to each other, without specifying any particular type of relationship. In other embodiments, relation annotations may also indicate specific types of relations between entity mentions. Any suitable number and/or types of relation annotations may be used, as aspects of the present disclosure are not limited in this respect. For example, in some embodiments, one type of relation annotation may be a "split" relation label. The tokens "sinusitis" and "chronic," for example, may be labeled as having a split relationship, because "sinusitis" and "chronic" together make up an entity, even though they are not contiguous within the text. In this case, "sinusitis" and "chronic" together indicate a specific type of sinusitis fact, i.e., one that it is chronic and not, e.g., acute. Another illustrative type of relation may be an "attribute" relation. In some embodiments, one or more system developers may define sets of attributes for particular fact types, corresponding to related information that may be specified for a fact type. For example, a "Medication" fact type may have attributes "dosage," "route," "frequency," "duration," etc. In another example, an "Allergy" fact type may have attributes "allergen," "reaction," "severity," etc. It should be appreciated, however, that the foregoing are merely examples, and that aspects of the present disclosure are not limited to any particular attributes for any particular fact types. Also, other types of fact relations are possible, including family relative relations, causes-problem relations, improves-problem relations, and many others. Aspects of the present disclosure are not limited to use of any particular relation types.

In some embodiments, using techniques similar to those described above, the labeled training text may be used as input to train the statistical relation model by extracting features from the text, and probabilistically associating the extracted features with the manually supplied labels. Any suitable set of features may be used, as aspects of the present disclosure are not limited in this respect. For example, in some embodiments, features used by a statistical relation model may include entity (e.g., fact type) labels, parts of speech, parser features, N-gram features, token window size (e.g., a count of the number of words or tokens present between two tokens that are being related to each other), and/or any other suitable features. It should be appreciated, however, that the foregoing features are merely illustrative, as embodiments are not limited to any particular list of features. In some embodiments, rather than outputting only the best (e.g., most probable) hypothesis for relations between entity mentions, a statistical relation model may output a list of multiple alternative hypotheses, e.g., with corresponding probabilities, of how the entity mentions labeled in the input text are related to each other. In yet other embodiments, a relation model may be hard-coded and/or otherwise rule-based, while the entity detection model used to label text portions with fact types may be trained statistically.

In some embodiments, the relation model or another statistical model may also be trained to track mentions of the same entity from different sentences and/or document sections and to relate them together. Illustrative techniques for entity tracking are described in the publication by Florian cited above.

In some embodiments, further processing may be applied to normalize particular facts extracted from the text to standard forms and/or codes in which they are to be documented. For example, medical personnel often have many different ways of phrasing the same medical fact, and a normalization/coding process in some embodiments may be applied to identify the standard form and/or code corresponding to each extracted medical fact that was stated in a non-standard way. The standard form and/or code may be derived from any suitable source, as aspects of the present disclosure are not limited in this respect. Some standard terms and/or codes may be derived from a government or profession-wide standard, such as SNOMED (Systematized Nomenclature of Medicine), UMLS (Unified Medical Language System), RxNorm, RadLex, etc. Other standard terms and/or codes may be more locally derived, such as from standard practices of a particular locality or institution. Still other standard terms and/or codes may be specific to the documentation system including the fact extraction component being applied.

For example, given the input text, "His sinuses are constantly inflamed," in some embodiments, an entity detection model together with a relation model (or a single model performing both functions) may identify the tokens "sinuses," "constantly" and "inflamed" as representing a medical fact. In some embodiments, a normalization/coding process may then be applied to identify the standard form for documenting "constantly inflamed sinuses" as "sinusitis, chronic." Alternatively or additionally, in some embodiments the normalization/coding process may identify a standard code used to document the identified fact. For example, the ICD-9 code for "sinusitis, chronic" is ICD-9 code #473. Any suitable coding system may be used, as aspects of the present disclosure are not limited in this respect. Illustrative standard codes include ICD (International Classification of Diseases) codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes.

In some embodiments, a normalization/coding process may be rule-based (e.g., using lists of possible ways of phrasing particular medical facts, and/or using an ontology of medical terms and/or other language units to normalize facts extracted from input text to their standard forms). For example, in some embodiments, the tokens identified in the text as corresponding to a medical fact may be matched to corresponding terms in an ontology. In some embodiments, a list of closest matching terms may be generated, and may be ranked by their similarity to the tokens in the text. The similarity may be scored in any suitable way. For example, in one suitable technique, one or more tokens in the text may be considered as a vector of its component elements, such as words, and each of the terms in the ontology may also be considered as a vector of component elements such as words. Similarity scores between the tokens may then be computed by comparing the corresponding vectors, e.g., by calculating the angle between the vectors, or a related measurement such as the cosine of the angle. In some embodiments, one or more concepts that are linked in the ontology to one or more of the higher ranking terms (e.g., the terms most similar to the identified tokens in the text) may then be identified as hypotheses for the medical fact to be extracted from that portion of the text. Illustrative techniques that may be used in some embodiments are described in Salton, Wong & Yang: "A vector space model for automatic indexing," *Communications of the ACM*, November 1975. This publication is incorporated herein by reference in its entirety. However, these are merely examples, and any suitable technique(s) for normalizing entity tokens to standard terms may be utilized in some embodiments, as aspects of the present disclosure are not limited in this respect.

In some embodiments, the normalization/coding process may output a single hypothesis for the standard form and/or code corresponding to each extracted fact. For example, the single output hypothesis may correspond to the concept linked in the ontology to the term that is most similar to the token(s) in the text from which the fact is extracted. However, in other embodiments, the normalization/coding process may output multiple alternative hypotheses, e.g., with corresponding probabilities, for the standard form and/or code corresponding to an individual extracted fact. Thus, it should be appreciated that in some embodiments multiple alternative hypotheses for a medical fact to be extracted from a portion of input text may be identified by fact extraction component 104. Such alternative hypotheses may be collected at any or all of various processing levels of fact extraction, including entity detection, entity relation, and/or normalization/coding stages. In some embodiments, the list of alternative hypotheses may be thresholded at any of the various levels, such that the final list output by fact extraction component 104 may represent the N-best alternative hypotheses for a particular medical fact to be extracted.

It should be appreciated that the foregoing are merely examples, and that fact extraction component 104 may be implemented in any suitable way and/or form, as aspects of the present disclosure are not limited in this respect.

As discussed above, in some embodiments a statistical fact extraction model may use membership in one or more dictionaries as a feature for characterizing a token and determining whether it is part of a mention of an entity of interest. For example, the fact that the token "sinusitis" is a member of a dictionary of types of inflammation may make it more likely that "sinusitis" represents a "Problem" entity in the input text. Thus, in one example, when a set of features is being extracted for the token "sinusitis," a search may be conducted to determine whether "sinusitis" is a member of any relevant predefined dictionaries. When it is determined that "sinusitis" is a member of the "inflammation" dictionary, a "member of inflammation dictionary" feature may be included in the extracted set of features for the token "sinusitis." In general, a dictionary useful as a feature for a statistical model typically is a list of terms that fall under the common heading of the dictionary; usually, the terms listed in dictionary "X" are all "types of X." For example, the "inflammation" dictionary may consist of a list of terms for types of inflammation, such as "arthritis," "asthma," "celiac disease," "colitis," "fibromyalgia," "meningitis," "tendonitis," etc. In some embodiments, a statistical entity detection model may have learned a probability that tokens belonging to a particular dictionary are associated with a particular entity label. For example, the entity detection model may have learned that tokens in the "inflammation" dictionary have a probability $P_{problem}$ of being labeled as "Problem" entity mentions, based on the frequency with which tokens in the "inflammation" dictionary were hand-labeled as "Problem" entity mentions in the training corpus. When tasked with automatically labeling the input token "sinusitis," the statistical model may consider this probability associated with membership in the "inflammation" dictionary, together with other probabilities learned for other features of "sinusitis," and may combine the probabilities of all those features to determine a likelihood that "sinusitis" should be labeled as a "Problem" entity mention. In some cases, a token may be a member of more than one dictionary, and then more than one dictionary feature may be extracted for that token. For example, "sinusitis" could be a member of both an "inflammation" dictionary and a "respiratory system conditions" dictionary, and the statistical model may have learned for each of these dictionaries a different probability of corresponding to a "Problem" entity. In this example, both dictionary features may be extracted for the token "sinusitis," and the associated probabilities for both features may be considered (e.g., suitably weighted and combined) in evaluating the likelihood that "sinusitis" should be labeled as a "Problem" entity mention.

Although dictionary membership may be a useful feature in entity detection and other statistical modeling techniques, accurate and complete predefined dictionaries are not often easy to come by, and often do not provide adequate coverage for many tokens that need to be labeled. For example, it could be useful to the entity detection task to know that "sinusitis" is a type of condition that occurs in an area of the head, but there may not be a dictionary available for "head-related conditions," or there may be a dictionary that includes some "head-related conditions" but is incomplete in that it does not include "sinusitis" for some reason. In such a situation, there may be no available feature that can be extracted for "sinusitis" to capture the knowledge that it is a head-related condition. Additionally, some predefined dictionaries may be overinclusive, in that one or more of their members do not actually belong in the categorization defined by the dictionary, when the token is considered in the classification task at hand. For example, the medical term "truncus arteriosus" appears in a publicly available dictionary of "body sites," but usually is used by physicians to denote a disorder, and not a body site, when documenting a patient encounter. (This is because the truncus arteriosus, when present in the heart, is a congenital defect.) The predefined dictionary of "body sites" may thus be detrimental to use as a feature for the token "truncus arteriosus" when it appears in a physician's report, since the dictionary feature may bias the statistical model toward labeling the token as a "Body Site," when it actually should be labeled as a "Disorder" or "Problem."

One possible solution to the above-recognized difficulties arising from reliance on dictionary features may be to manually construct task-specific dictionaries for every different type of entity detection task that may arise. However, such a process would be time-consuming and often impractical, would likely require a significant amount of expert knowledge and foresight as to exactly what terms would be encountered in input texts and exactly how they should be classified, and as such might defeat many of the advantages of employing statistical machine learning techniques as opposed to solely hand-coded rule-based models. Accordingly, alternative techniques are developed to replace or supplement the use of dictionary features in statistical entity detection and fact extraction. These alternative techniques may make use of knowledge, related to the classification of terms and/or their relationships with other known concepts, that is not easily reflected in pre-constructed dictionaries.

In some embodiments, one or more ontologies may be used to access multiple levels of known classifications of concepts relevant to terms in an input text, and/or to access other known relationships between relevant concepts that can aid in the fact extraction process. As used herein, the term "ontology" refers to any knowledge representation (which may be encoded and/or stored in any suitable data format) that includes representations of known concepts and of known relationships between those concepts. An ontology is often represented graphically as a set of nodes connected to each other by edges, with each node representing a concept and each edge connecting two nodes representing a relationship between the concepts represented by those two nodes. Any concept about which there is human knowledge can be represented as a node in an ontology, and any type of known relationship between concepts can be represented as an edge in an ontology. One type of concept relationship is a parent-child relationship (also referred to herein as a hypernym-hyponym relationship, or an "is-a" relationship), but other types of concept relationships may also be represented in ontologies, as discussed further below. A particular ontology may include multiple types of concept relationships. However, some particular types of ontologies may be more restricted, e.g., to only one type or certain types of concept relationships. For example, one particular type of ontology is a taxonomy, which includes only parent-child relationships. Any type of ontology (including, for example, a taxonomy) may be used with techniques described herein, as aspects of the present disclosure are not limited to the use of any particular type of ontology.

Illustrative techniques for entity detection, including illustrative techniques that make use of one or more ontologies linked to one or more lexicons of medical terms are described in U.S. patent application Ser. No. 13/795,886, filed on Mar. 13, 2013, entitled "Methods and Apparatus for Entity Detection," which is incorporated herein by reference in its entirety.

In some embodiments, a user such as clinician 120 may monitor, control and/or otherwise interact with the fact extraction and/or fact review process through a user interface provided in connection with system 100. For example, in some embodiments, user interface 140 may be provided by fact review component 106, e.g., through execution (e.g., by one or more processors of system 100) of programming instructions incorporated in fact review component 106. One exemplary implementation of such a user interface is graphical user interface (GUI). In some embodiments, when the user is clinician 120, GUI may be presented via user interface 110. In some embodiments, a user may be a person other than a clinician; for example, another person such as coding specialist 150 may be presented with GUI via user interface 140.

Figure 11:
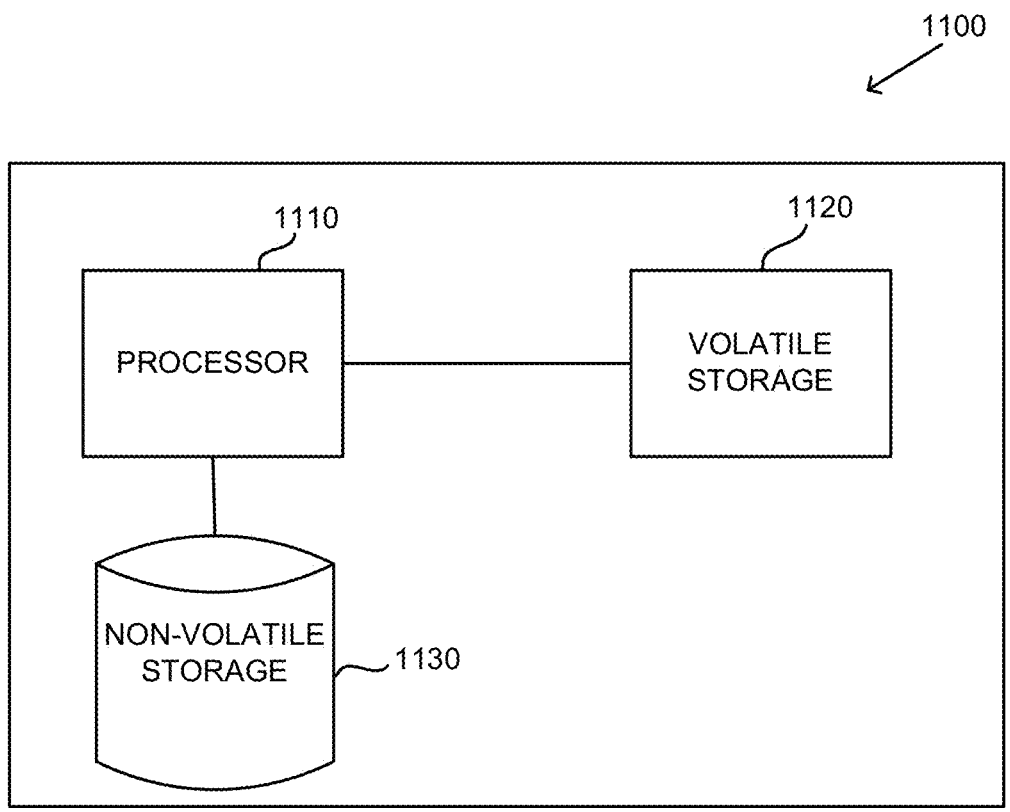
FIG. 11 shows an illustrative computer system on which aspects of the present disclosure may be implemented, in accordance with some embodiments.

A system in accordance with the techniques described herein may take any suitable form, as aspects of the present disclosure are not limited in this respect. An illustrative implementation of a computer system 1100 that may be used in connection with some embodiments of the present disclosure is shown in FIG. 11. One or more computer systems such as computer system 1100 may be used to implement any of the functionality described above. The computer system 1100 may include one or more processors 1110 and one or more tangible, non-transitory computer-readable storage media (e.g., volatile storage 1120 and one or more non-volatile storage media 1130, which may be formed of any suitable non-volatile data storage media). The processor 1110 may control writing data to and reading data from the volatile storage 1120 and the non-volatile storage device 1130 in any suitable manner, as the aspects of the present disclosure are not limited in this respect. To perform any of the functionality described herein, the processor 1110 may execute one or more instructions stored in one or more computer-readable storage media (e.g., volatile storage 1120), which may serve as tangible, non-transitory computer-readable storage media storing instructions for execution by the processor 1110.

The above-described embodiments of the present disclosure can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present disclosure comprises at least one computer-readable storage medium (i.e., a tangible, non-transitory computer-readable medium, such as a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present disclosure. The computer-readable storage medium can be transportable such that the program stored thereon can be loaded onto any computer resource to implement aspects of the present disclosure discussed herein. In addition, it should be appreciated that the reference to a computer program which, when executed, performs any of the above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present disclosure.

The phraseology and terminology used herein is for the purpose of description and should not be regarded as limiting. The use of "including," "comprising," "having," "containing", "involving", and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements from each other.

Having described several embodiments of the disclosure in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A system comprising at least one processor and at least one storage medium storing executable instructions, the at least one processor being programmed by the executable instructions to perform a method for verifying compliance of medical documentation with at least one medical guideline for care of a patient and/or documenting the care of the patient, the method comprising acts of:

evaluating a medical recommendation of a medical professional with respect to a patient encounter to determine whether the medical recommendation is consistent with at least one medical guideline, wherein evaluating the medical recommendation to determine whether the medical recommendation is consistent with the at least one medical guideline comprises:

analyzing, using at least one natural language understanding engine, at least one narrative provided by the medical professional in connection with an examination of the patient, wherein the at least one natural language understanding engine uses a machine learning technique selected from the group consisting of maximum entropy modeling, support vector machines, and random fields, wherein the machine learning technique is trained on a training corpus of hand-annotated medical documentation that includes previously-identified extracted features and entity labels describing facts, and wherein analyzing, using the at least one natural language understanding engine, the at least one narrative comprises extracting, using the at least one natural language understanding engine, one or more facts from the at least one narrative provided by the medical professional;

determining, using the one or more facts extracted by the at least one natural language understanding engine from the at least one narrative, whether the medical recommendation is consistent with the at least one medical guideline, wherein determining whether the medical recommendation is consistent with the at least one medical guideline comprises:

applying one or more decision rules to the one or more facts extracted by the at least one natural language understanding engine from the at least one narrative, the one or more decision rules comprising a first decision rule relating to at least one item of information and at least one recommendation called for by at least a first medical guideline of the at least one medical guideline, and wherein applying the one or more decision rules comprises determining, via application of the first decision rule, whether the medical professional provided in the at least one narrative the at least one item of information called for by at least the first medical guideline;

in response to determining that the medical professional did not provide in the at least one narrative at least a first item of information, of the at least one item of information called for by at least the first medical guideline:

automatically selecting an assumed value from a plurality of possible values to use for the first item of information that was not provided by the medical professional;

applying at least the first decision rule to the one or more facts and the at least one assumed value to determine whether the medical recommendation is consistent with the at least one recommendation called for by at least the first medical guideline;

presenting the assumed value for the first item of information that was not provided by the medical professional incorporated in a draft report comprising the at least one narrative for confirmation of the assumed value by the medical professional; and in response to receiving a correction to the assumed value for the first item of information that was not provided by the medical professional:

determining which of the one or more decision rules relates to the first item of information that was not provided by the medical professional, and reapplying at least one decision rule of the one or more decision rules that was determined to relate to the first item of information that was not provided by the medical professional, wherein the reapplying comprises applying the at least one decision rule to at least a portion of a second draft report, the at least the portion of the second draft report comprising the correction and not comprising the assumed value, and wherein reapplying the at least one decision rule comprises, in response to determining that the first decision rule of the one or more decision rules relates to the first item of information that was not provided by the medical professional, reapplying the first decision rule to the at least the portion of the second draft report to determine whether the medical recommendation is consistent with the at least one recommendation called for by at least the first medical guideline.

2. The system of claim 1, wherein the one or more decision rules comprises a decision rule for determining whether the at least one medical guideline is applicable to a study, the decision rule being the first decision rule or another decision rule.

3. The system of claim 1, wherein the one or more decision rules comprises a decision rule for determining whether the medical professional failed to provide a recommendation called for by the at least one medical guideline, the decision rule being the first decision rule or another decision rule.

4. The system of claim 1, wherein applying the one or more decision rules comprises:

generating, in response to applying at least the first decision rule, an alert for alerting the medical professional of at least one incomplete and/or inconsistent medical recommendation, and outputting for presentation, via a graphical user interface, the alert and an identification of one or more medical guidelines corresponding to at least the first decision rule that triggered the alert.

5. The system of claim 1, wherein automatically selecting the assumed value comprises identifying and selecting from among the plurality of possible values a value based on a demographic of which the patient is a member, wherein identifying and selecting the value comprises:

identifying and selecting the value based on statistical likelihoods of the plurality of possible values for the demographic of which the patient is a member.

6. The system of claim 4, wherein the method further comprises:
   determining an alternative medical recommendation consistent with the at least one recommendation called for by at least the first medical guideline; and
   outputting for presentation the alternative medical recommendation via the graphical user interface.

7. The system of claim 1, wherein the method further comprises:
   generating a formatted report based on the one or more facts extracted from the at least one narrative, wherein the formatted report indicates that an inconsistent medical recommendation was made in the at least one narrative by the medical professional responsive to a determination that the medical recommendation is inconsistent with the at least one recommendation called for by at least the first medical guideline.

8. The system of claim 1, wherein the method further comprises:
   determining an initial recommendation, called for by at least the first medical guideline, based at least in part on the assumed value; and
   reapplying the first decision rule further comprises:
      determining an updated recommendation, called for by at least the first medical guideline, based at least in part on the correction to the assumed value for the first item of information and a result of reapplying the first decision rule to the at least the portion of the second draft report, and
      determining whether the medical recommendation is consistent with the updated recommendation called for by at least the first medical guideline.

9. The system of claim 8, wherein the method further comprises:
   presenting the updated recommendation to the medical professional, wherein the updated recommendation is visually linked to the correction.

10. The system of claim 1, wherein:
    the one or more decision rules comprises a second decision rule; and
    applying the one or more decision rules comprises applying the second decision rule; and
    the method further comprises, in response to receiving the correction to the assumed value for the first item of information and determining that the second decision rule does not relate to the first item of information that was not provided by the medical professional, refraining from reapplying the second decision rule of the one or more decision rules to the at least the portion of the second draft report.

11. The system of claim 1, wherein the medical professional is a radiologist and the method further comprises:
    analyzing, using the at least one natural language understanding engine, the at least one narrative provided by the radiologist in connection with examination of one or more medical images of the patient.

12. The system of claim 5, wherein selecting the value comprises selecting a first value that is more likely than a second value for the demographic and not more likely than the second value for another demographic, the plurality of possible values including the first value and the second value.

13. The system of claim 1, wherein the one or more decision rules are generated based on one or more medical guidelines, and the method further comprises:
    updating the one or more decision rules based on new or modified medical guidelines,
    wherein applying the one or more decision rules comprises applying the updated one or more decision rules to the one or more facts extracted by the at least one natural language understanding engine from the at least one narrative.

14. A method for verifying compliance of medical documentation with at least one medical guideline for care of a patient and/or documenting the care of the patient, the method comprising acts of:
    evaluating a medical recommendation of a medical professional with respect to a patient encounter to determine whether the medical recommendation is consistent with at least one medical guideline, wherein evaluating the medical recommendation to determine whether the medical recommendation is consistent with the at least one medical guideline comprises:
       analyzing, using at least one natural language understanding engine, at least one narrative provided by the medical professional in connection with an examination of the patient, wherein the at least one natural language understanding engine uses a machine learning technique selected from the group consisting of maximum entropy modeling, support vector machines, and random fields, wherein the machine learning technique is trained on a training corpus of hand-annotated medical documentation that includes previously-identified extracted features and entity labels describing facts, and wherein analyzing, using the at least one natural language understanding engine, the at least one narrative comprises extracting, using the at least one natural language understanding engine, one or more facts from the at least one narrative provided by the medical professional;
    using at least one processor to determine, using the one or more facts extracted by the at least one natural language understanding engine from the at least one narrative, whether the medical recommendation is consistent with the at least one medical guideline, wherein determining whether the medical recommendation is consistent with the at least one medical guideline comprises:
       applying one or more decision rules to the one or more facts extracted by the at least one natural language understanding engine from the at least one narrative, the one or more decision rules comprising a first decision rule that relates to at least one item of information and at least one recommendation called for by at least a first medical guideline of the at least one medical guideline, and wherein applying the one or more decision rules comprises determining, via application of the first decision rule, whether the medical professional provided in the at least one narrative the at least one item of information called for by at least the first medical guideline;
       in response to the determining that the medical professional did not provide in the at least one narrative at least a first item of information, of the at least one item of information called for by at least the first medical guideline:

automatically selecting an assumed value from a plurality of possible values to use for the first item of information that was not provided by the medical professional;

applying at least the first decision rule to the one or more facts and the at least one assumed value to determine whether the medical recommendation is consistent with the at least one recommendation called for by at least the first medical guideline;

presenting the assumed value for the first item of information that was not provided by the medical professional incorporated in a draft report comprising the at least one narrative for confirmation of the assumed value by the medical professional; and in response to receiving a correction to the assumed value for the first item of information that was not provided by the medical professional:

determining which of the one or more decision rules relates to the first item of information that was not provided by the medical professional, and reapplying at least one decision rule of the one or more decision rules that was determined to relate to the first item of information that was not provided by the medical professional, wherein the reapplying comprises applying the at least one decision rule to at least a portion of a second draft report, the at least the portion of the second draft report comprising the correction and not comprising the assumed value, and wherein reapplying the at least one decision rule comprises, in response to determining that the first decision rule of the one or more decision rules relates to the first item of information that was not provided by the medical professional, reapplying the first decision rule to the at least the portion of the second draft report to determine whether the medical recommendation is consistent with the at least one recommendation called for by at least the first medical guideline.

15. The method of claim 14, wherein the one or more decision rules comprises a decision rule for determining whether the at least one medical guideline is applicable to a study, the decision rule being the first decision rule or another decision rule.

16. The method of claim 14, wherein the one or more decision rules comprises a decision rule for determining whether the medical professional failed to provide a recommendation called for by the at least one medical guideline, the decision rule being the first decision rule or another decision rule.

17. The method of claim 14, wherein applying the one or more decision rules comprises:

generating, in response to applying at least the first decision rule, an alert for alerting the medical professional of at least one incomplete and/or inconsistent medical recommendation, and outputting for presentation, via a graphical user interface, the alert and an identification of one or more medical guidelines corresponding to at least the first decision rule that triggered the alert.

18. The method of claim 14, further comprising an act of: generating a formatted report based on the one or more facts extracted from the at least one narrative, wherein the formatted report indicates that an inconsistent medical recommendation was made in the at least one narrative by the medical professional responsive to a determination that the medical recommendation is inconsistent with the at least one recommendation called for by at least the first medical guideline.

19. At least one non-transitory computer-readable storage medium having stored thereon instructions that, when executed by at least one processor, perform a method for verifying compliance of medical documentation with at least one medical guideline for care of a patient and/or documenting the care of the patient, the method comprising acts of:

evaluating a medical recommendation of a medical professional with respect to a patient encounter to determine whether the medical recommendation is consistent with at least one medical guideline, wherein evaluating the medical recommendation to determine whether the medical recommendation is consistent with the at least one medical guideline comprises:

analyzing, using at least one natural language understanding engine, at least one narrative provided by the medical professional in connection with an examination of the patient, wherein the at least one natural language understanding engine uses a machine learning technique selected from the group consisting of maximum entropy modeling, support vector machines, and random fields, wherein the machine learning technique is trained on a training corpus of hand-annotated medical documentation that includes previously-identified extracted features and entity labels describing facts, and wherein analyzing, using the at least one natural language understanding engine, the at least one narrative comprises extracting, using the at least one natural language understanding engine, one or more facts from the at least one narrative provided by the medical professional;

determining, using the one or more facts extracted by the at least one natural language understanding engine from the at least one narrative, whether the medical recommendation is consistent with the at least one medical guideline, wherein determining whether the medical recommendation is consistent with the at least one medical guideline comprises:

applying one or more decision rules to the one or more facts extracted by the at least one natural language understanding engine from the at least one narrative, the one or more decision rules comprising a first decision rule that relates to at least one item of information and at least one recommendation called for by at least a first medical guideline of the at least one medical guideline, and wherein applying the one or more decision rules comprises determining, via application of the first decision rule, whether the medical professional provided in the at least one narrative the at least one item of information called for by at least the first medical guideline; and in response to the determining that the medical professional did not provide in the at least one narrative at least a first item of information, of the at least one item of information called for by at least the first medical guideline:

automatically selecting an assumed value from a plurality of possible values to use for the first item of information that was not provided by the medical professional;

applying at least the first decision rule to the one or more facts and the at least one assumed value to determine whether the medical recommendation is consistent with the at least one recommendation called for by at least the first medical guideline;

presenting the assumed value for the first item of information that was not provided by the medical professional incorporated in a draft report comprising the at least one narrative for confirmation of the assumed value by the medical professional; and in response to receiving the correction to the assumed value for the first item of information that was not provided by the medical professional:
  determining which of the one or more decision rules relates to the first item of information that was not provided by the medical professional, and
  reapplying at least one decision rule of the one or more decision rules that was determined to relate to the first item of information that was not provided by the medical professional, wherein the reapplying comprises applying the at least one decision rule to at least a portion of a second draft report, the at least the portion of the second draft report comprising the correction and not comprising the assumed value, and wherein reapplying the at least one decision rule comprises, in response to determining that the first decision rule of the one or more decision rules relates to the first item of information that was not provided by the medical professional, reapplying the first decision rule to the at least the portion of the second draft report to determine whether the medical recommendation is consistent with the at least one recommendation called for by at least the first medical guideline.

20. The at least one non-transitory computer-readable storage medium of claim 19, wherein applying the one or more decision rules comprises:
  generating, in response to applying at least the first decision rule, an alert for alerting the medical professional of at least one incomplete and/or inconsistent medical recommendation, and
  outputting for presentation, via a graphical user interface, the alert and an identification of one or more medical guidelines corresponding to at least the first decision rule that triggered the alert.

* * * * *